US010870710B2

(12) United States Patent
DiGiandomenico et al.

(10) Patent No.: US 10,870,710 B2
(45) Date of Patent: Dec. 22, 2020

(54) SYNTHETIC OLIGOSACCHARIDE SUBUNITS OF THE PSL EXOPOLYSACCHARIDE OF PSEUDOMONAS AERUGINOSA AND USES THEREOF

(71) Applicants: MedImmune Limited, Cambridge (GB); University Of Georgia Research Foundation, Inc., Athens, GA (US)

(72) Inventors: Antonio DiGiandomenico, Gaithersburg, MD (US); Qun Wang, Gaithersburg, MD (US); Charles K. Stover, Gaithersburg, MD (US); Geert-Jan Boons, Athens, GA (US); Kai-For Mo, Athens, GA (US); Huiqing Li, Athens, GA (US)

(73) Assignees: MedImmune Limited, Cambridge (GB); University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 16/219,199

(22) Filed: Dec. 13, 2018

(65) Prior Publication Data
US 2019/0309095 A1    Oct. 10, 2019

Related U.S. Application Data

(63) Continuation of application No. 14/890,205, filed as application No. PCT/US2014/037839 on May 13, 2014, now abandoned.

(60) Provisional application No. 61/823,009, filed on May 14, 2013.

(51) Int. Cl.
| | | |
|---|---|---|
| C08B 37/00 | (2006.01) | |
| C07H 15/04 | (2006.01) | |
| G01N 33/569 | (2006.01) | |
| A61K 47/64 | (2017.01) | |
| A61K 39/104 | (2006.01) | |
| G01N 33/53 | (2006.01) | |
| A61K 39/00 | (2006.01) | |

(52) U.S. Cl.
CPC ........ *C08B 37/0006* (2013.01); *A61K 39/104* (2013.01); *A61K 47/643* (2017.08); *A61K 47/646* (2017.08); *C07H 15/04* (2013.01); *G01N 33/5308* (2013.01); *G01N 33/56911* (2013.01); *A61K 2039/6081* (2013.01); *G01N 2333/21* (2013.01); *G01N 2400/00* (2013.01); *G01N 2400/02* (2013.01); *G01N 2400/38* (2013.01); *G01N 2500/04* (2013.01)

(58) Field of Classification Search
CPC .......... C08B 37/0006; A61K 47/646; A61K 47/643; A61K 39/104; A61K 2039/6081; C07H 15/04; G01N 33/56911; G01N 33/5308

USPC ......................................................... 536/124
See application file for complete search history.

(56) References Cited

U.S. PATENT DOCUMENTS

2016/0115250 A1    4/2016   DiGiandomenico et al.

FOREIGN PATENT DOCUMENTS

| WO | WO-2012/125626 A2 | 9/2012 |
|---|---|---|
| WO | 2012145626 A1 | 10/2012 |
| WO | WO-2012/145626 A1 | 10/2012 |
| WO | WO-2012/170807 A2 | 12/2012 |
| WO | 2013070615 A1 | 5/2013 |
| WO | WO-2013/070615 A1 | 5/2013 |

OTHER PUBLICATIONS

Digiandomenico et al., "Identification of broadly protective human antibodies to Pseudomonas aeruginosa exopolysaccharide Psi by phenotypic screening.", J Exp Med. 2012, vol. 209(7), p. 1273-87.
Li et a l. "Epitope Mapping of Monoclonal Antibodies using Synthetic Oligosaccharides Uncovers Novel Aspects of Immune Recognition of the Psi Exopolysaccharide of Pseudomonas aeruginosa," Chem Eur J, vol. 19, pp. 17425-17431, Nov. 18, 2013 (Nov. 18, 2013).
Fdanklin et al. "Biosynthesis of the Pseudomonas aeruginosa extracellular polysaccharides, alginate, Pel, and Psi," Frontiers in Microbiology vol. 2, Article 167, pp. 1-16, Aug. 22, 2011 (Aug. 22, 2011).
Colvin et a I. "The Pel and Psi polysaccharides provide Pseudomonas aeruginosa structural redundancy within the biofilm matrix," Environ Microbiol, vol. 14, No. 8, pp. 1-26, Aug. 2012.
Ma et al. "Pseudomonas aeruginosa Psi is a Galactose- and Mannose-Rich Exopolysaccharide" Journal of Bacteriology, vol. 189, No. 22, pp. 8353-8356, Jul. 13, 2007 (Jul. 13, 2007).
Alonsodevelasco E et al: "*Streptococcus pneumoniae*: Virulence Factors, Pathogenesis, and Vaccines", Microbiological Reviews, American Society for Microbiology, Washington, DC, US, vol. 59, No. 4, Dec. 1, 1995 (Dec. 1, 1995 ), pp. 591-603.
Kim JS et al: "Determination of saccharide content in pneumococcal polysaccharides and conjugate vaccines by GC-MSD", Analytical Biochemistry, Elsevier, Amsterdam, NL, vol. 347, No. 2, Dec. 15, 2005 (Dec. 15, 2005), pp. 262-274.

(Continued)

*Primary Examiner* — Shaojia A Jiang
*Assistant Examiner* — Michael C Henry
(74) *Attorney, Agent, or Firm* — Sterne, Kessler, Goldstein & Fox P.L.L.C.

(57) ABSTRACT

This disclosure relates to synthetic oligosaccharide subunits of the *Pseudomonas* exosaccharide Psi and uses thereof, e.g., for epitope mapping of anti-Psl antibodies, for identification of anti-Psl antibodies, and for use as vaccines. In one aspect a synthetic oligosaccharide subunit of a *Pseudomonas aeruginosa* Psl oligosaccharide is provided, comprising the trisaccharide of formula I.

Figure 2:
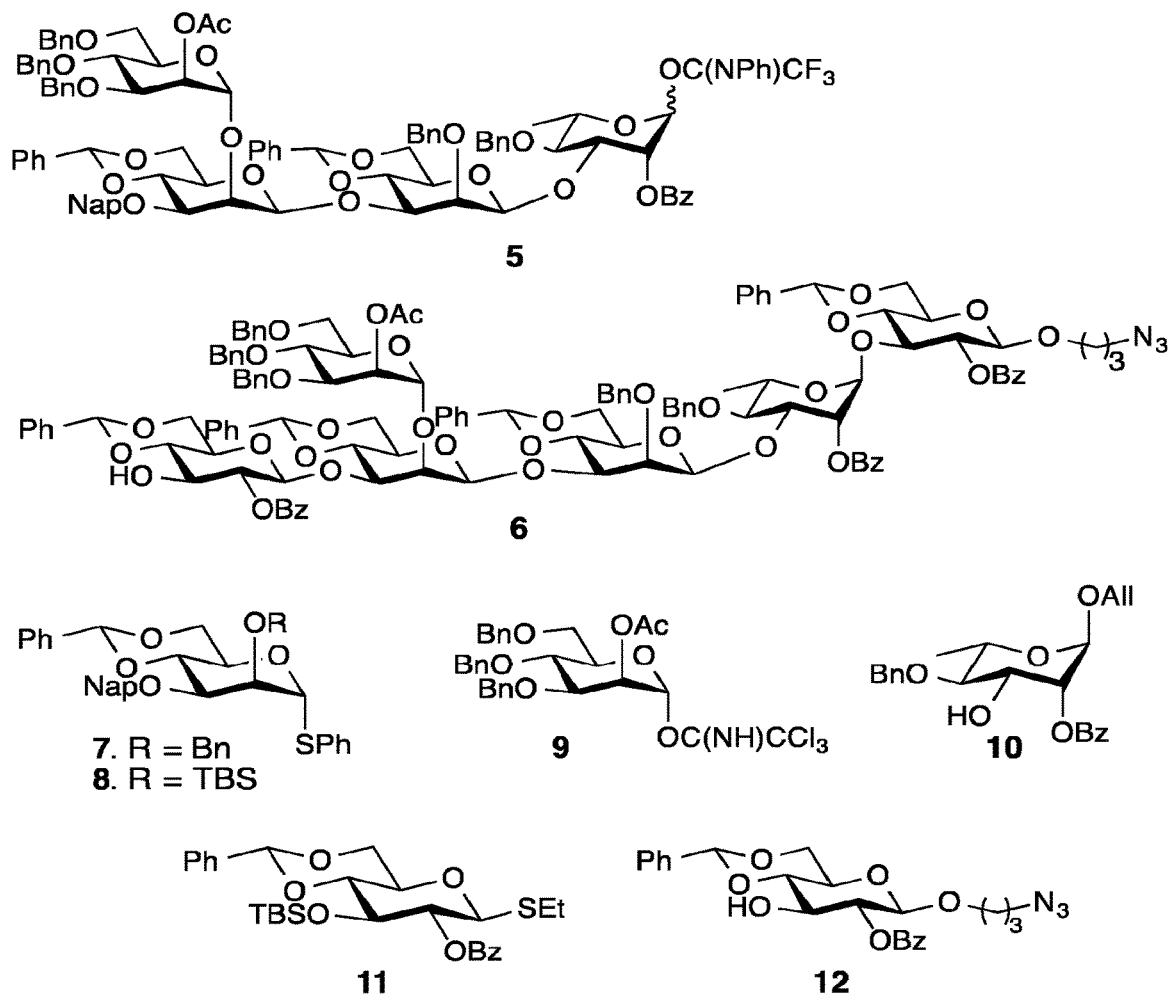

7 Claims, 3 Drawing Sheets
Specification includes a Sequence Listing.

(56) References Cited

OTHER PUBLICATIONS

Vliegenthart et al: "Carbohydrate based vaccines", FEBS Letters, Elsevier, Amsterdam, NL, vol. 580, No. 12, May 22, 2006 (May 22, 2006), pp. 2945-2950.

AlonsoDeVelasco et al., *Streptococcus pneumoniae*: virulence factors, pathogenesis, and vaccines, Microbiol. Rev., 59(4):591-60 (Dec. 1995).

Byrd et al., Genetic and biochemical analyses of the Pseudomonas aeruginosa Psl exopolysaccharide reveal overlapping roles for polysaccharide synthesis enzymes in Psl and LPS production, Mol. Microbiol., 73(4):622-38 (Aug. 2009).

Chinese Patent Application No. 201480022945.1, First Office Action, dated Nov. 19, 2018.

Colvin et al., The Pel and Psl polysaccharides provide Pseudomonas aeruginosa structural redundancy within the biofilm matrix, Environ. Microbiol., 14(8):1913-28 (Aug. 2012).

Digiandomenico et al., "Identification of broadly protective human antibodies to Pseudomonas aeruginosa axopolysaccharide Psl by phenotypic screening.", J Exp Med. 2012, vol. 209(7), p. 1273-87.

European patent application No. 14797588.2, Extended European Search Report, dated Jan. 10, 2017.

Franklin et al., Biosynthesis of the Pseudomonas aeruginosa Extracellular Polysaccharides, Alginate, Pel, and Psl, Front Microbiol., 2:167 (Aug. 2011).

International Application No. PCT/US2014/037839, International Preliminary Report on Patentability, dated Nov. 17, 2015.

International Application No. PCT/US2014/037839, International Search Report and Written Opinion, dated Nov. 5, 2014.

Japanese patent application No. 2016-514031, Decision of Refusal, dated Aug. 16, 2018.

Japanese patent application No. 2016-514031, Notification of Reasons for Refusal, dated Dec. 21, 2017.

Kim et al., Determination of saccharide content in pneumococcal polysaccharides and conjugate vaccines by GC-MSD, Anal. Biochem., 347(2):262-74 (Dec. 1995).

Li et al., "Epitope Mapping of Monoclonal Antibodies using Synthetic Oligosaccharides Uncovers Novel Aspects of mmune Recognition of the Psl Exopolysaccharide of Pseudomonas aeruginosa," Chem Eur J, vol. 19, pp. 17425-17431, Nov. 18, 2013 (Nov. 18, 2013).

Ma et al., Pseudomonas aeruginosa Psl is a galactose- and mannose-rich exopolysaccharide, J. Bacteriol., 189(22):8353-6 (Nov. 2007).

Vliegenthart, Carbohydrate based vaccines, FEBS Lett., 580(12):2945-50 (May 2006).

FIGURE 1A-B
a.  repeating unit of Psl of *P. aeruginosa*
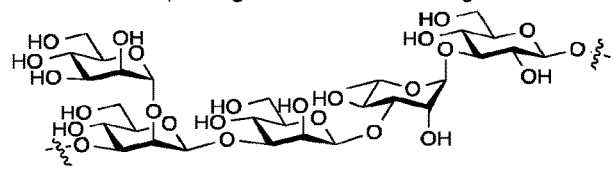
b. Synthetic target oligosaccharides
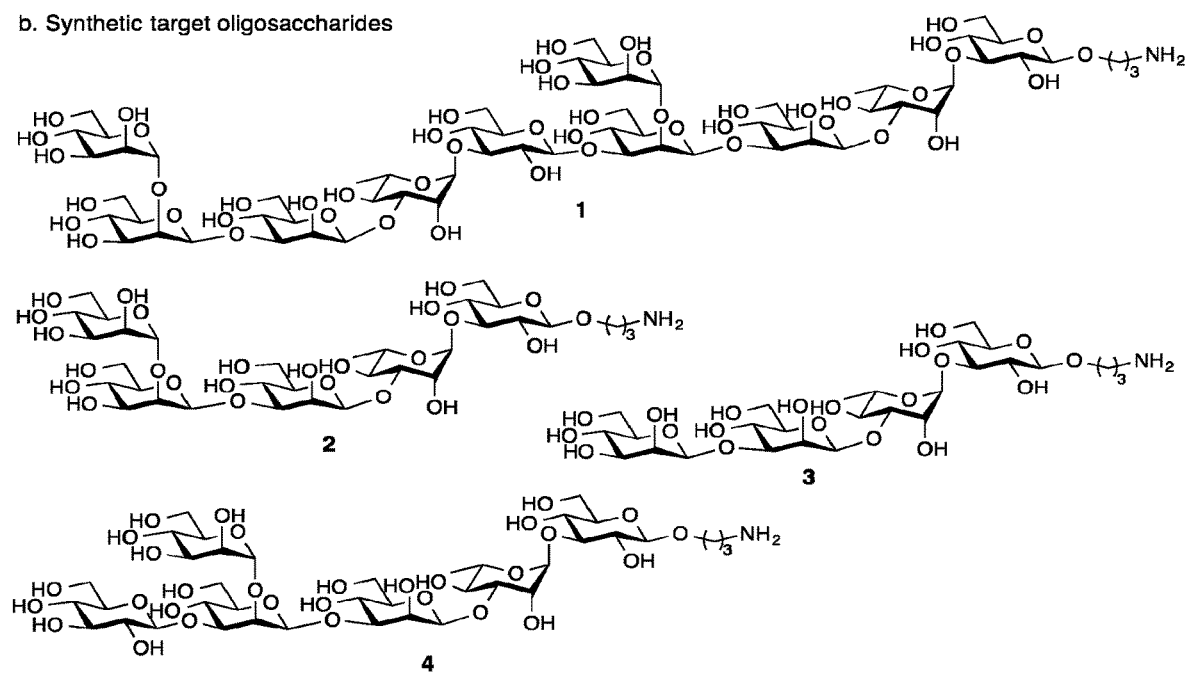
Figure 1. Structure of the repeating unit of the exopolysaccharide of *P. aeruginosa* and target compounds for chemical synthesis Figure 2. Building blocks for oligosaccharide assembly FIGURE 3A-D
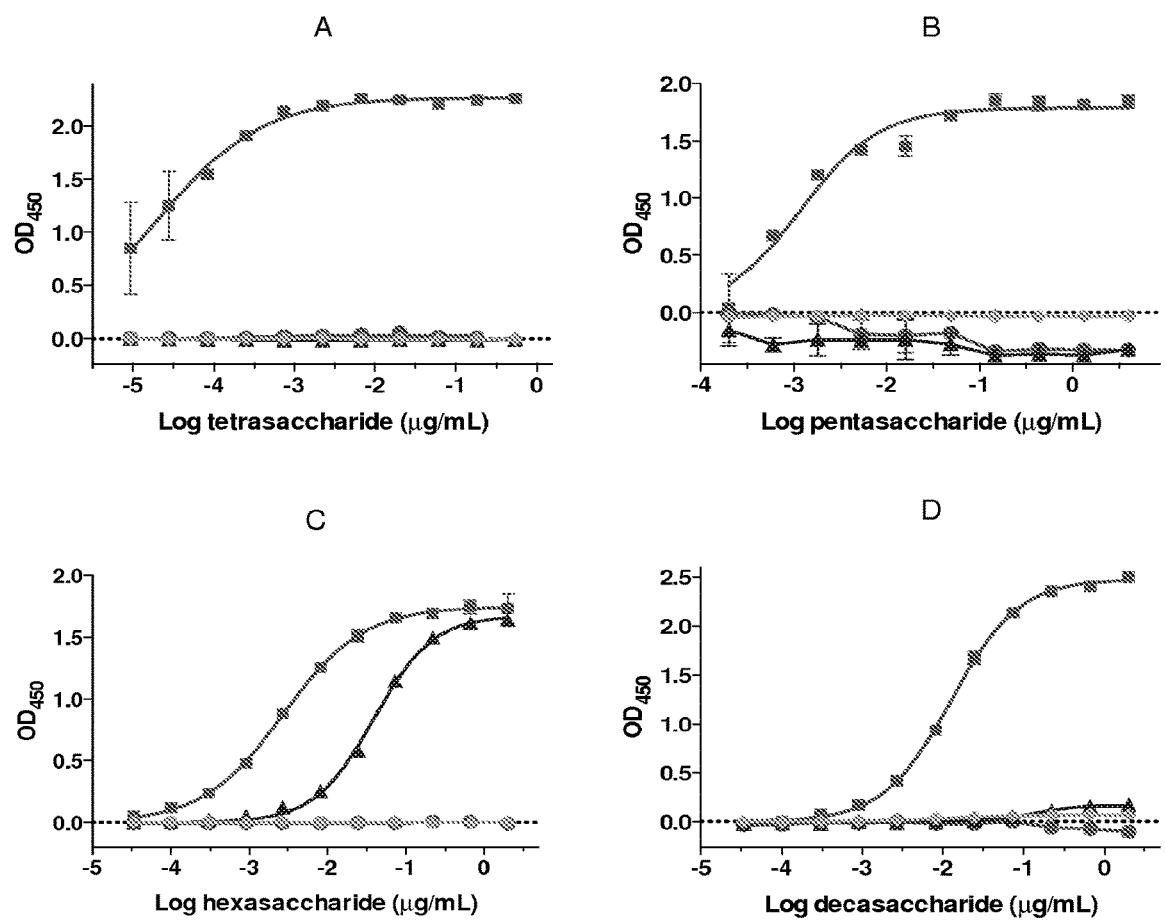

```
                        SEQUENCE LISTING

<160> NUMBER OF SEQ ID NOS: 12

<210> SEQ ID NO 1
<211> LENGTH: 118
<212> TYPE: PRT
<213> ORGANISM: Artificial
<220> FEATURE:
<223> OTHER INFORMATION: Cam-003 VH

<400> SEQUENCE: 1

Gln Val Arg Leu Gln Gln Ser Gly Pro Gly Leu Val Lys Pro Ser Glu
1               5                   10                  15

Thr Leu Ser Leu Thr Cys Thr Val Ser Gly Gly Ser Thr Ser Pro Tyr
            20                  25                  30

Phe Trp Ser Trp Leu Arg Gln Pro Pro Gly Lys Gly Leu Glu Trp Ile
        35                  40                  45

Gly Tyr Ile His Ser Asn Gly Gly Thr Asn Tyr Asn Pro Ser Leu Lys
    50                  55                  60

Ser Arg Leu Thr Ile Ser Gly Asp Thr Ser Lys Asn Gln Phe Ser Leu
65                  70                  75                  80

Asn Leu Ser Phe Val Thr Ala Ala Asp Thr Ala Leu Tyr Tyr Cys Ala
                85                  90                  95

Arg Thr Asp Tyr Asp Val Tyr Gly Pro Ala Phe Asp Ile Trp Gly Gln
            100                 105                 110

Gly Thr Met Val Thr Val
        115

<210> SEQ ID NO 2
<211> LENGTH: 108
<212> TYPE: PRT
<213> ORGANISM: Artificial
<220> FEATURE:
<223> OTHER INFORMATION: Cam-003, Cam-004, and Cam-005 VL

<400> SEQUENCE: 2

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
```

```
                      85                  90                  95

Val Val Phe Gly Gly Gly Thr Lys Leu Thr Val Leu
                100                 105

<210> SEQ ID NO 3
<211> LENGTH: 118
<212> TYPE: PRT
<213> ORGANISM: Artificial
<220> FEATURE:
<223> OTHER INFORMATION: Cam-004 VH

<400> SEQUENCE: 3

Gln Val Gln Leu Gln Gln Ser Gly Pro Gly Arg Val Lys Pro Ser Glu
1               5                   10                  15

Thr Leu Ser Leu Thr Cys Thr Val Ser Gly Tyr Ser Val Ser Ser Gly
                20                  25                  30

Tyr Tyr Trp Gly Trp Ile Arg Gln Ser Pro Gly Thr Gly Leu Glu Trp
            35                  40                  45

Ile Gly Ser Ile Ser His Ser Gly Ser Thr Tyr Tyr Asn Pro Ser Leu
        50                  55                  60

Lys Ser Arg Val Thr Ile Ser Gly Asp Ala Ser Lys Asn Gln Phe Phe
65                  70                  75                  80

Leu Arg Leu Thr Ser Val Thr Ala Ala Asp Thr Ala Val Tyr Tyr Cys
                85                  90                  95

Ala Arg Ser Glu Ala Thr Ala Asn Phe Asp Ser Trp Gly Arg Gly Thr
                100                 105                 110

Leu Val Thr Val Ser Ser
            115

<210> SEQ ID NO 4
<211> LENGTH: 119
<212> TYPE: PRT
<213> ORGANISM: Artificial
<220> FEATURE:
<223> OTHER INFORMATION: Cam-005 VH

<400> SEQUENCE: 4

Gln Val Gln Leu Gln Gln Ser Gly Pro Gly Leu Val Lys Pro Ser Glu
1               5                   10                  15

Thr Leu Ser Leu Thr Cys Thr Val Ser Gly Gly Ser Val Ser Ser Ser
                20                  25                  30

Gly Tyr Tyr Trp Thr Trp Ile Arg Gln Pro Pro Gly Lys Gly Leu Glu
            35                  40                  45

Trp Ile Gly Ser Ile Tyr Ser Ser Gly Ser Thr Tyr Tyr Ser Pro Ser
        50                  55                  60

Leu Lys Ser Arg Val Thr Ile Ser Gly Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Leu Asn Trp Gly Thr Val Ser Ala Phe Asp Ile Trp Gly
                100                 105                 110

Arg Gly Thr Leu Val Thr Val
            115

<210> SEQ ID NO 5
<211> LENGTH: 119
<212> TYPE: PRT
<213> ORGANISM: Artificial
<220> FEATURE:
```

<223> OTHER INFORMATION: WapR-001 VH

<400> SEQUENCE: 5

Glu Val Gln Leu Leu Glu Ser Gly Gly Gly Leu Val Gln Pro Gly Gly
1               5                   10                  15

Ser Leu Arg Leu Ser Cys Ser Ala Ser Gly Phe Thr Phe Ser Arg Tyr
            20                  25                  30

Pro Met His Trp Val Arg Gln Ala Pro Gly Lys Gly Leu Glu Tyr Val
        35                  40                  45

Ser Asp Ile Gly Thr Asn Gly Gly Ser Thr Asn Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Ser Ser Leu Arg Ala Glu Asp Thr Ala Val Tyr His Cys
                85                  90                  95

Val Ala Gly Ile Ala Ala Ala Tyr Gly Phe Asp Val Trp Gly Gln Gly
            100                 105                 110

Thr Met Val Thr Val Ser Ser
        115

<210> SEQ ID NO 6
<211> LENGTH: 110
<212> TYPE: PRT
<213> ORGANISM: Artificial
<220> FEATURE:
<223> OTHER INFORMATION: WapR-001 VL

<400> SEQUENCE: 6

Gln Ala Gly Leu Thr Gln Pro Ala Ser Val Ser Gly Ser Pro Gly Gln
1               5                   10                  15

Ser Ile Thr Ile Ser Cys Thr Gly Thr Ser Ser Asp Ile Ala Thr Tyr
            20                  25                  30

Asn Tyr Val Ser Trp Tyr Gln Gln His Pro Gly Lys Ala Pro Lys Leu
        35                  40                  45

Met Ile Tyr Glu Gly Thr Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Arg Ser
                85                  90                  95

Tyr Thr Tyr Val Phe Gly Thr Gly Thr Glu Leu Thr Val Leu
            100                 105                 110

<210> SEQ ID NO 7
<211> LENGTH: 118
<212> TYPE: PRT
<213> ORGANISM: Artificial
<220> FEATURE:
<223> OTHER INFORMATION: WapR-002 VH

<400> SEQUENCE: 7

Gln Val Gln Leu Val Gln Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Pro Met His Trp Val Arg Gln Ala Pro Gly Lys Gly Leu Asp Tyr Val
        35                  40                  45

Ser Asp Ile Ser Pro Asn Gly Gly Ser Thr Asn Tyr Ala Asp Ser Val

```
                50                  55                  60
Lys Gly Arg Phe Thr Ile Ser Arg Asp Asn Ser Lys Asn Thr Leu Phe
 65                  70                  75                  80

Leu Gln Met Ser Ser Leu Arg Ala Glu Asp Thr Ala Val Tyr Tyr Cys
                 85                  90                  95

Val Met Gly Leu Val Pro Tyr Gly Phe Asp Ile Trp Gly Gln Gly Thr
                100                 105                 110

Leu Val Thr Val Ser Ser
            115
```

<210> SEQ ID NO 8
<211> LENGTH: 110
<212> TYPE: PRT
<213> ORGANISM: Artificial
<220> FEATURE:
<223> OTHER INFORMATION: WapR-002 VL

<400> SEQUENCE: 8

```
Gln Thr Val Val Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
            35                  40                  45

Met Ile Tyr Glu Val Ser Asn Arg Pro Ser Gly Val Ser Asn His Phe
         50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Thr Thr Ser
                 85                  90                  95

Ser Thr Tyr Val Phe Gly Thr Gly Thr Lys Val Thr Val Leu
                100                 105                 110
```

<210> SEQ ID NO 9
<211> LENGTH: 118
<212> TYPE: PRT
<213> ORGANISM: Artificial
<220> FEATURE:
<223> OTHER INFORMATION: WapR-003 VH

<400> SEQUENCE: 9

```
Gln Met Gln Leu Val Gln Ser Gly Gly Gly Leu Val Gln Pro Gly Gly
 1               5                  10                  15

Ser Leu Arg Leu Ser Cys Ser Ala Ser Gly Phe Thr Phe Ser Ser Tyr
                20                  25                  30

Pro Met His Trp Val Arg Gln Ala Pro Gly Lys Gly Leu Asp Tyr Val
            35                  40                  45

Ser Asp Ile Ser Pro Asn Gly Gly Ala Thr Asn Tyr Ala Asp Ser Val
         50                  55                  60

Lys Gly Arg Phe Thr Ile Ser Arg Asp Asn Ser Lys Asn Thr Val Tyr
 65                  70                  75                  80

Leu Gln Met Ser Ser Leu Arg Ala Glu Asp Thr Ala Val Tyr Tyr Cys
                 85                  90                  95

Val Met Gly Leu Val Pro Tyr Gly Phe Asp Asn Trp Gly Gln Gly Thr
                100                 105                 110

Met Val Thr Val Ser Ser
            115
```

<210> SEQ ID NO 10
<211> LENGTH: 110
<212> TYPE: PRT
<213> ORGANISM: Artificial
<220> FEATURE:
<223> OTHER INFORMATION: WapR-003 VL

<400> SEQUENCE: 10

Gln Thr Val Val Thr Gln Pro Ala Ser Val Ser Ala Ser Pro Gly Gln
1               5                   10                  15

Ser Ile Thr Ile Ser Cys Ala Gly Thr Ser Gly Asp Val Gly Asn Tyr
            20                  25                  30

Asn Phe Val Ser Trp Tyr Gln Gln His Pro Gly Lys Ala Pro Lys Leu
        35                  40                  45

Leu Ile Tyr Glu Gly Ser Gln Arg Pro Ser Gly Val Ser Asn Arg Phe
    50                  55                  60

Ser Gly Ser Arg Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Arg Ser
                85                  90                  95

Tyr Thr Tyr Val Phe Gly Thr Gly Thr Lys Leu Thr Val Leu
            100                 105                 110

<210> SEQ ID NO 11
<211> LENGTH: 123
<212> TYPE: PRT
<213> ORGANISM: Artificial
<220> FEATURE:
<223> OTHER INFORMATION: WapR-016 VH

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Ser Tyr
            20                  25                  30

Ala Thr Ser Trp Val Arg Gln Ala Pro Gly Lys Gly Leu Glu Trp Val
        35                  40                  45

Ala Gly Ile Ser Gly Ser Gly Asp Thr Thr Asp Tyr Val Asp Ser Val
    50                  55                  60

Lys Gly Arg Phe Thr Val Ser Arg Asp Asn Ser Lys Asn Thr Leu Tyr
65                  70                  75                  80

Leu Gln Met Asn Ser Leu Arg Ala Asp Asp Thr Ala Val Tyr Tyr Cys
                85                  90                  95

Ala Ser Arg Gly Gly Leu Gly Gly Tyr Tyr Arg Gly Gly Phe Asp Phe
            100                 105                 110

Trp Gly Gln Gly Thr Met Val Thr Val Ser Ser
        115                 120

<210> SEQ ID NO 12
<211> LENGTH: 108
<212> TYPE: PRT
<213> ORGANISM: Artificial
<220> FEATURE:
<223> OTHER INFORMATION: WapR-016 VL

<400> SEQUENCE: 12

Gln Ser Val Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr

|  | 20 |  |  | 25 |  |  |  | 30 |  |  |  |  |
|---|---|---|---|---|---|---|---|---|---|---|---|---|
| Asn | Tyr | Val | Ser | Trp | Tyr | Gln | Gln | His | Pro | Gly | Lys | Ala | Pro | Lys | Leu |
|  |  | 35 |  |  |  | 40 |  |  |  |  | 45 |  |  |  |  |
| Met | Ile | Tyr | Glu | Val | Ser | Asn | Arg | Pro | Ser | Gly | Val | Ser | Asn | Arg | Phe |
|  | 50 |  |  |  |  | 55 |  |  |  |  | 60 |  |  |  |  |
| Ser | Gly | Ser | Lys | Ser | Gly | Asn | Thr | Ala | Ser | Leu | Thr | Ile | Ser | Gly | Leu |
| 65 |  |  |  |  | 70 |  |  |  |  | 75 |  |  |  |  | 80 |
| Gln | Ala | Glu | Asp | Glu | Ala | Asp | Tyr | Cys | Ser | Ser | Tyr | Ser | Ser | Gly | Thr |
|  |  |  |  | 85 |  |  |  |  | 90 |  |  |  |  | 95 |  |
| Val | Val | Phe | Gly | Gly | Gly | Thr | Glu | Leu | Thr | Val | Leu |  |  |  |  |
|  |  |  | 100 |  |  |  |  | 105 |  |  |  |  |  |  |  |

SYNTHETIC OLIGOSACCHARIDE SUBUNITS OF THE PSL EXOPOLYSACCHARIDE OF PSEUDOMONAS AERUGINOSA AND USES THEREOF

CROSS REFERENCE TO RELATED APPLICATIONS

This application is a continuation of U.S. application Ser. No. 14/890,205, filed Nov. 10, 2015, which is the national phase entry of International Application No. PCT/US2014/037839, filed May 13, 2014, which claims the priority benefit of U.S. Provisional Application No. 61/823,009, filed May 14, 2013.

REFERENCE TO A SEQUENCE LISTING SUBMITTED ELECTRONICALLY VIA EFS-WEB

The content of the electronically submitted sequence listing (Name: 2018-12-12-PSEUD-102-US-CNT-Seqlisting.txt; Size: 13,356 bytes; and Date of Creation: Dec. 12, 2018) is herein incorporated by reference in its entirety.

BACKGROUND

Field of the Disclosure

This disclosure relates to an anti-*Pseudomonas* Psl binding molecules and uses thereof, in particular in prevention and treatment of *Pseudomonas* infection. Furthermore, the disclosure provides compositions and methods for preventing and treating *Pseudomonas* infection.

Background of the Disclosure

*Pseudomonas aeruginosa* (*P. aeruginosa*) is a gram-negative opportunistic pathogen that causes both acute and chronic infections in compromised individuals (Ma et al., *Journal of Bacteriology* 189(22):8353-8356 (2007)). This is partly due to the high innate resistance of the bacterium to clinically used antibiotics, and partly due to the formation of highly antibiotic-resistant biofilms (Drenkard E., *Microbes Infect* 5:1213-1219 (2003); Hancock & Speert, *Drug Resist Update* 3:247-255 (2000)).

*P. aeruginosa* is a common cause of hospital-acquired infections in the Western world. It is a frequent causative agent of bacteremia in burn victims and immune compromised individuals (Lyczak et al., *Microbes Infect* 2:1051-1060 (2000)). It is also the most common cause of nosocomial gram-negative pneumonia (Craven et al., *Semin Respir Infect* 11:32-53 (1996)), especially in mechanically ventilated patients, and is the most prevalent pathogen in the lungs of individuals with cystic fibrosis (Pier et al., *ASM News* 6:339-347 (1998)). Serious *P. aeruginosa* infections can become systemic, resulting in sepsis. Sepsis is characterized by severe systemic inflammation, often resulting in multiple organ failure and death.

*Pseudomonas* Psl exopolysaccharide is reported to be anchored to the surface of *P. aeruginosa* and is thought to be important in facilitating colonization of host tissues and in establishing/maintaining biofilm formation (Jackson, K. D., et al., *J Bacteriol* 186, 4466-4475 (2004)). Its structure comprises mannose-rich repeating pentasaccharide (Byrd, M. S., et al., *Mol Microbiol* 73, 622-638 (2009))

Due to increasing multidrug resistance, there remains a need in the art for the development of novel strategies for the identification of new *Pseudomonas*-specific prophylactic and therapeutic agents.

PCT/US2012/041538, filed Jun. 8, 2012 (incorporated herein by reference in its entirety), describes monoclonal antibodies (mAbs) that specifically bind to the serotype-independent Psl exopolysaccharide. See also DiGiandomenico, A. et al. (2012) *J Exp Med* 209:1273-87, incorporated herein by reference in its entirety. The antibodies were classified into three groups (class I, II, and III) based on competitive binding assays. Antibodies that bound the class I and II epitopes were non-competitive with each other, while the lone antibody targeting the class III epitope, WapR-016, partially competed with antibodies targeting the class I and II epitopes. A survey of anti-Psl mAbs binding to *P. aeruginosa* clinical isolates indicated Psl expression/accessibility among 85% of all isolates tested (147/173) with greater reactivity observed from isolates obtained from confirmed acute infections (96%). These results indicate that Psl is a novel serotype-independent protective antigen that is surface accessible and prevalent among non-mucoid and mucoid clinical isolates.

There remains a need in the art to identify the regions of Psl which bind the class I, II, and III anti-Psl Mabs, in order to generate and screen new antibodies, and for use as a vaccine component.

BRIEF SUMMARY

This disclosure provides synthetic oligosaccharide subunits of *Pseudomonas* Psl oligosaccharides.

In one aspect a synthetic oligosaccharide subunit of a *Pseudomonas aeruginosa* Psl oligosaccharide is provided, comprising the trisaccharide of formula I.

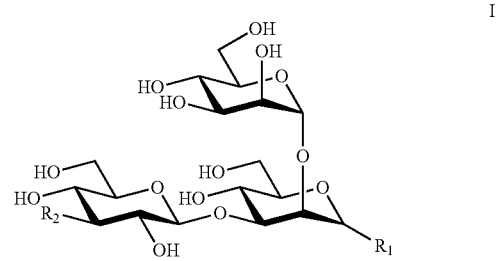

According to this aspect. $R_1$ can be —OH or

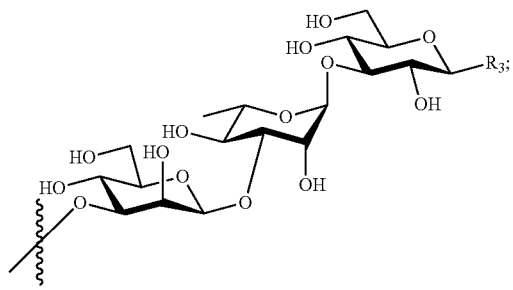

$R_2$ can be —OH or

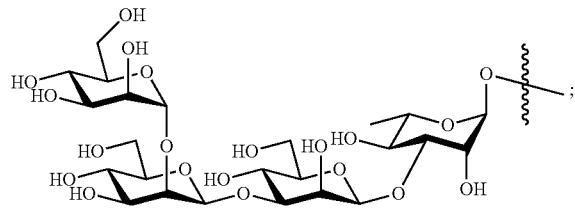

and $R_3$ can be —OX, where X is hydrogen, an alkyl group, or an aryl group; a linker, wherein the linker can be —O—$(CH_2)_n$—$NH_2$, —O—$(CH_2)_n$—COOH, —O—$(CH_2)_n$—$N_3$, —O—$(CH_2)_n$—$S(CH_2)_m$—$NH_2$, —O—$(CH_2)_n$—$S(CH_2)_m$—COOH, —O—$(CH_2)_n$—$S(CH_2)_m$—$N_3$, —O—$(CH_2)_n$—$SO_2(CH_2)_m$—$NH_2$, —O—$(CH_2)_n$—$SO_2(CH_2)_m$—COOH, or —O—$(CH_2)_n$—$SO_2(CH_2)_m$—$N_3$, wherein n and m are the same or different and are independently 0, 1, 2, 3, 4, 5, 6, 7, 8, 9, or 10; or a linker coupled to a heterologous moiety via conjugation, wherein the heterologous moiety can be a protein, a lipid or a polymer. The oligosaccharide subunit according to this aspect can be specifically bound by the anti-Psl monoclonal antibody WapR-016, or an antigen binding fragment thereof.

In certain aspects the oligosaccharide subunit of of Formula I, comprises the hexasaccharide:

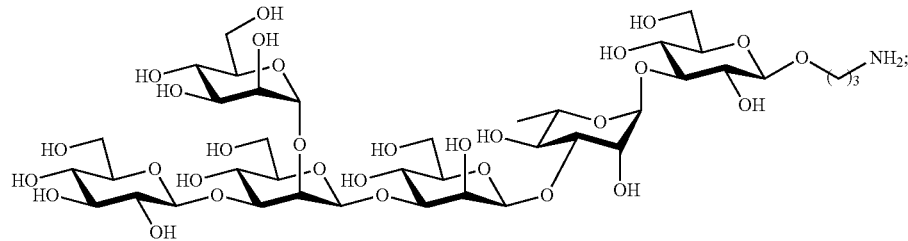

or the decasaccharide:

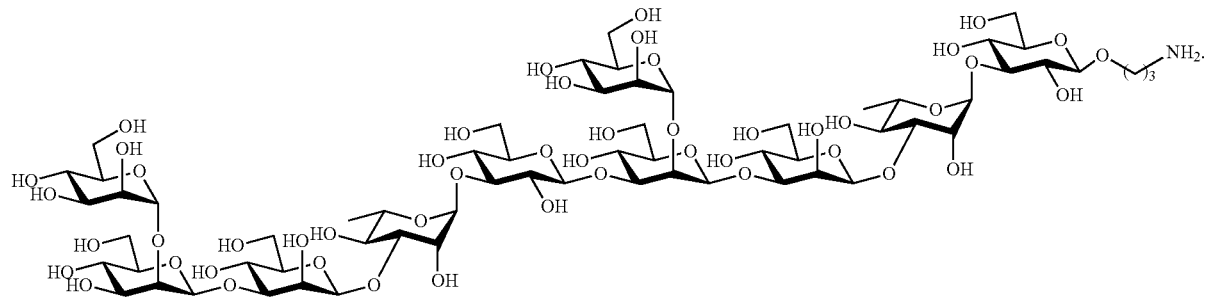

In certain aspects, the monoclonal antibody WapR-016 which can specifically bind to the oligosaccharide subunit of Formula I comprises VH and VL amino acid sequences of SEQ ID NO:11 and SEQ ID NO: 12, respectively.

In another aspect a synthetic oligosaccharide subunit of a *Pseudomonas aeruginosa* Psl oligosaccharide is provided, comprising the tetrasaccharide of formula II:

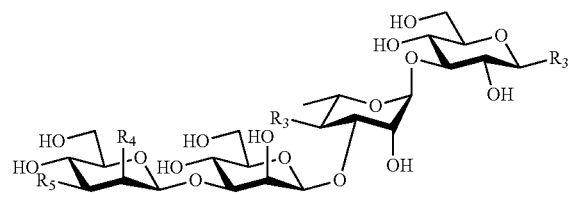

According to this aspect, $R_4$ can be —OH or

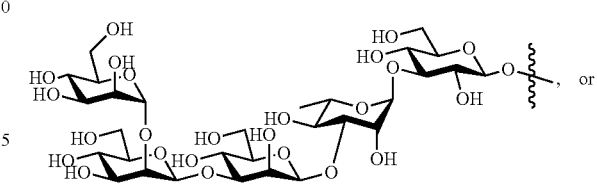

$R_5$ can be —OH,

, or

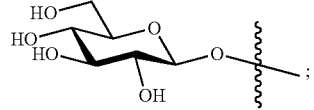

and $R_3$ can be —OX, where X is hydrogen, an alkyl group, or an aryl group; a linker, wherein the linker can be —O—$(CH_2)_n$—$NH_2$, —O—$(CH_2)_n$—COOH, —O—$(CH_2)_n$—$N_3$, —O—$(CH_2)_n$—$S(CH_2)_m$—$NH_2$, —O—$(CH_2)_n$—$S(CH_2)_m$—COOH, —O—$(CH_2)_n$—$S(CH_2)_m$—$N_3$, —O—$(CH_2)_n$—$SO_2(CH_2)_m$—$NH_2$, —O—$(CH_2)_n$—$SO_2(CH_2)_m$—COOH, or —O—$(CH_2)_n$—$SO_2(CH_2)_m$—$N_3$, where n and m are the same or different and are independently 0, 1, 2, 3, 4, 5, 6, 7, 8, 9, or 10; or a linker coupled to a heterologous moiety via conjugation, wherein the heterologous moiety can be a protein, a lipid or a polymer. The oligosaccharide subunit according to this aspect can be specifically bound by the anti-Psl monoclonal antibody WapR-001, or an antigen binding fragment thereof.

In certain aspects the oligosaccharide subunit of of Formula II, comprises the tetrasaccharide:

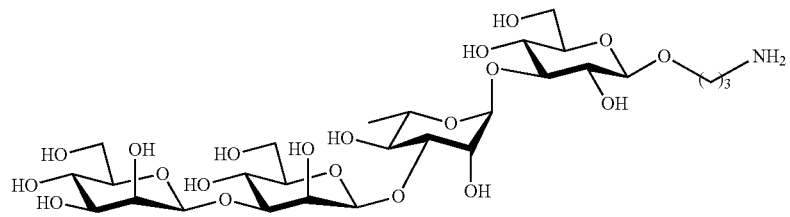

the pentasaccharide:

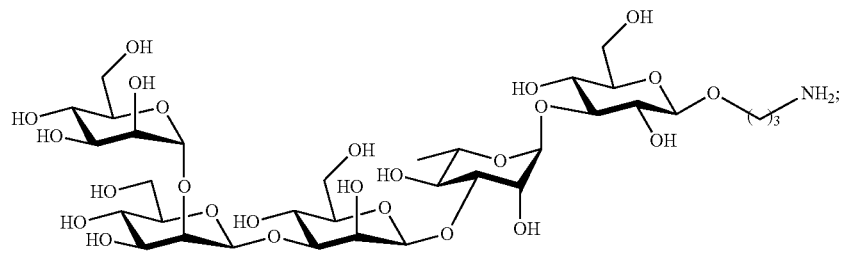

the hexasaccharide:

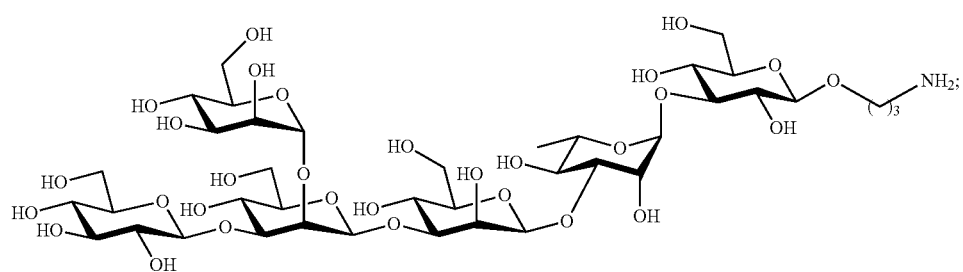

or the decasaccharide:

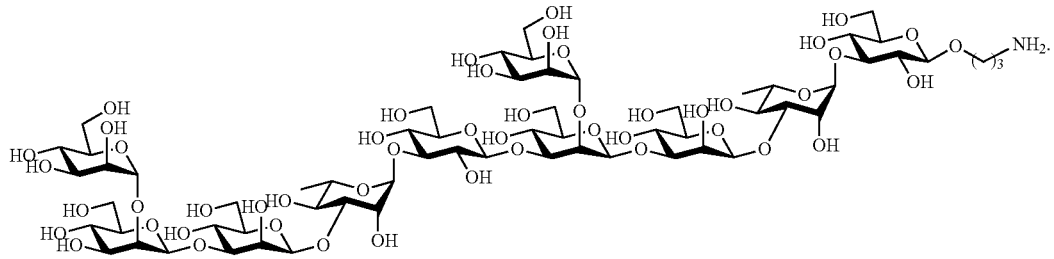

In certain aspects, the monoclonal antibody WapR-016 does not bind to the tetrasaccharide or pentasaccharide shown above.

In certain aspects, the monoclonal antibody WapR-001 which can specifically bind to the oligosaccharide subunit of Formula II comprises VH and VL amino acid sequences of SEQ ID NO:5 and SEQ ID NO:6, respectively.

In certain aspects, any of the oligosaccharide subunits provided herein can be conjugated to a polypeptide, a lipid, or a polymer. In certain aspects the polypeptide can be albumin, e.g., bovine serum albumin or human serum albumin.

The disclosure further provides of method of evaluating the binding characteristics of an anti-*Pseudomonas aeruginosa* Psl antibody or antigen-binding fragment thereof to *Pseudomonas aeruginosa* Psl epitope. In certain aspects the method comprises (a) contacting the antibody with an oligosaccharide subunit as provided herein under conditions that allow the antibody to bind the oligosaccharide subunit; and (b) detecting the presence of a complex of the antibody and the oligosaccharide subunit. In certain aspects the complex is detected by an immunoassay, e.g., an ELISA assay. In certain aspects the method can further comprise: (c) classifying the antibody as binding to a class II epitope if it binds to each of the tetrasaccharide, pentasaccharide, hexasaccharide, and decasaccharide described above; and/or (d) classifying the antibody as binding to a class II epitope if it binds to the hexasaccharide or decasaccharide described above, but does not bind to the tetrasaccharide or the pentasaccharide described above.

The disclosure further provides of method of screening for antibodies which bind to *Pseudomonas aeruginosa* Psl. In certain aspects the method comprises (a) contacting an antibody or antibody fragment library with an oligosaccharide subunit as provided herein under conditions that allow Psl-specific antibodies or fragments thereof to hind the oligosaccharide subunit; (b) detecting the presence of a complex of the antibody and the oligosaccharide subunit; and (c) selecting antibodies which bind to the oligosaccharide subunit. In certain aspects the complex is detected by an immunoassay, e.g., an ELISA assay.

The disclosure further provides compositions, e.g., pharmaceutical compositions comprising an oligosaccharide subunit as provided herein for use, e.g., as a vaccine.

BRIEF DESCRIPTION OF THE DRAWINGS/FIGURES

FIG. 1A shows the basic repeating structure of the Psl oligosaccharide of *Pseudomonas aeruginosa*. FIG. 1B shows the four synthetic oligosaccharide subunits used for Psl epitope mapping; compound 1 is the decasaccharide, compound 2 the pentasaccharide, compound 3 the tetrasaccharide, and compound 4 the hexasaccharide.

FIG. 2 shows the building blocks used to synthesize the compounds shown in FIG. 1B. The compound numbers refer to intermediate structures 1-12 are referred to in the synthetic schemes detailed in Example 1.

FIG. 3A-D shows anti-Psl mAb binding to synthetic Psl oligosaccharides. Microtiter plates were coated with tetrasaccharide (3)-BSA conjugate (3A), pentasaccharide (2)-BSA conjugate (3B), hexasaccharide (4)-BSA conjugate (3C), and decasaccharide (1)-BSA conjugate (3D) at the indicated carbohydrate concentrations. Anti-Psl mAbs class I (Cam-003, ●), class II (WapR-001, ■), class III (WapR-016, ▲), and R347 (♦) (5 µg/mL) were tested for reactivity with each oligosaccharide component. The optical density (OD) values are reported as the means±SD. Class I (Cam-003), II (WapR-001), and III (WapR-016) anti-Psl mAbs were previously shown to bind three unique epitopes of Psl derived from *P. aeruginosa*.

DETAILED DESCRIPTION

I. Definitions

It is to be noted that the term "a" or "an" entity refers to one or more of that entity; for example, "a binding molecule which specifically binds to *Pseudomonas* Psl," is understood to represent one or more binding molecules which specifically bind to *Pseudomonas* Psl. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systéme International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "oligosaccharide" refers to a molecule containing two or more monosaccharides. A monosaccharide is the basic building block of any carbohydrate. Monosaccharides have the basic molecular formula: $C_nH_{2n}O_n$, but often have substitutions. Oligosaccharides can be made by the methods described herein, or by methods known to those of skill in the art. The term "polysaccharide" can be used interchangeably with the term "oligosaccharide," but generally refers to relatively longer strings of monosaccharides.

The term "synthetic oligosaccharide" or "synthetic oligosaccharide subunit" refers to portions of an oligosaccharide, e.g., a naturally-occurring oligosaccharide, which has been produced by in vitro chemical synthesis. A oligosaccharide subunit, as used herein refers to an oligosaccharide, i.e., a molecule containing two or more monosaccharides, which can be a part of a larger oligosaccharide or a polysaccharide. For example, the *Pseudomonas aeruginosa* Psl oligosaccharide is reported to be composed of repeating subunits comprising five monosaccharides (see FIG. 1A).

The term "conjugate," as used herein, refers to synthetic oligosaccharides or oligosaccharide subunits that have been covalently coupled to a protein or other larger molecule, e.g., a lipid or a polymer, with a known biological activity through a linker. An oligosaccharide or oligosaccharide subunit can be conjugated, e.g., through an inter-glycosidic oxygen or sulfur.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide can be derived from a natural biological source or produced by recombinant technology, but is not necessarily translated from a designated nucleic acid sequence. It can be generated in any manner, including by chemical synthesis.

The terms "antibody" and "immunoglobulin" can be used interchangeably herein. An antibody (or a fragment, variant, or derivative thereof as disclosed herein comprises at least the variable domain of a heavy chain and at least the variable domains of a heavy chain and a light chain. Basic immunoglobulin structures in vertebrate systems are relatively well understood. See, e.g., Harlow et al., Antibodies: A Laboratory Manual, (Cold Spring Harbor Laboratory Press, 2nd ed. 1988).

Those skilled in the art will appreciate that heavy chains are classified as gamma, mu, alpha, delta, or epsilon, ($\gamma$, $\mu$, $\alpha$, $\delta$, $\epsilon$) with some subclasses among them (e.g., $\gamma 1$-$\gamma 4$). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgA_1$, etc. are well characterized and are known to confer functional specialization. Modified versions of each of these classes and isotypes are readily discernible to the skilled artisan in view of the instant disclosure and, accordingly, are within the scope of this disclosure.

Light chains are classified as either kappa or lambda ($\kappa$, $\lambda$). Each heavy chain class can be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows an antibody to selectively recognize and specifically bind epitopes on antigens. That is, the VL domain and VH domain, or subset of the complementarity determining regions (CDRs), of an antibody combine to form the variable region that defines a three dimensional antigen binding site. This quaternary structure forms the antigen binding site present at the end of each arm of the Y. More specifically, the antigen binding site is defined by three CDRs on each of the VH and VL chains.

Antibodies or antigen-binding fragments, variants, or derivatives thereof include, but are not limited to, polyclonal, monoclonal, human, humanized, or chimeric antibodies, single chain antibodies, epitope-binding fragments, e.g., Fab, Fab' and $F(ab')_2$, Fd, Fvs, single-chain Fvs (scFv), single-chain antibodies, disulfide-linked Fvs (sdFv), fragments comprising either a VL or VH domain, fragments produced by a Fab expression library. ScFv molecules are known in the art and are described, e.g., in U.S. Pat. No. 5,892,019.

By "specifically binds," it is generally meant that a binding molecule, e.g., an antibody or fragment, variant, or derivative thereof binds to an epitope via its antigen binding domain, and that the binding entails some complementarity between the antigen binding domain and the epitope.

According to this definition, a binding molecule is said to "specifically bind" to an epitope when it binds to that epitope, via its antigen binding domain more readily than it would bind to a random, unrelated epitope. The term "specificity" is used herein to qualify the relative affinity by which a certain binding molecule binds to a certain epitope. For example, binding molecule "A" may be deemed to have a higher specificity for a given epitope than binding molecule "B," or binding molecule "A" may be said to bind to epitope "C" with a higher specificity than it has for related epitope "D."

An antibody or fragment, variant, or derivative thereof is said to competitively inhibit binding of a reference antibody or antigen binding fragment to a given epitope if it preferentially binds to that epitope to the extent that it blocks, to some degree, binding of the reference antibody or antigen binding fragment to the epitope. Competitive inhibition can be determined by any method known in the art, for example, competition ELISA assays. A binding molecule can be said to competitively inhibit binding of the reference antibody or antigen binding fragment to a given epitope by at least 90%, at least 80%, at least 70%, at least 60%, or at least 50%.

As used herein, the term "affinity" refers to a measure of the strength of the binding of an individual epitope with the CDR of an immunoglobulin molecule. See, e.g., Harlow et al., Antibodies: A Laboratory Manual, (Cold Spring Harbor Laboratory Press, 2nd ed. 1988) at pages 27-28. As used herein, the term "avidity" refers to the overall stability of the complex between a population of immunoglobulins and an antigen, that is, the functional combining strength of an immunoglobulin mixture with the antigen. See, e.g., Harlow at pages 29-34. Avidity is related to both the affinity of individual antibody molecules in the population with specific epitopes, and also the valencies of the immunoglobulins and the antigen. For example, the interaction between a bivalent monoclonal antibody and an antigen with a highly repeating epitope structure, such as a polymer, would be one of high avidity.

As used herein, the terms "treat" or "treatment" refer to both therapeutic treatment and prophylactic or preventative measures, wherein the object is to prevent or slow down (lessen) an undesired physiological change, infection, or disorder. Beneficial or desired clinical results include, but are not limited to, alleviation of symptoms, diminishment of extent of disease, stabilized (i.e., not worsening) state of disease, clearance or reduction of an infectious agent such as *P. aeruginosa* in a subject, a delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the infection, condition, or disorder as well as those prone to have the condition or disorder or those in which the condition or disorder is to be prevented, e.g., in burn patients or immunosuppressed patients susceptible to *P. aeruginosa* infection.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, bears, and so on.

II. *Pseudomonas* Psl Oligosaccharides and Anti-Psl Antibodies

Psl facilitates the attachment of *P. aeruginosa* to epithelial cells in vivo and is essential for forming and maintaining biofilms (Digiandomenico, A., et al., *J. Exp. Med.* 2012, 209, 1273-1287; Hidron, A. I., et al., *Infect. Control Hosp. Epidemiol.* 2008, 29, 996-1011). In addition, Psl inhibits efficient opsonization, resulting in reduced neutrophil production of reactive oxygen species and decreased killing by phagocytic cells (Mishra, M., et al., *J. Cell. Microbiol.* 2012, 14, 95-106. Lectin staining and visualization of Psl on the surface of *P. aeruginosa* indicates that it is anchored to the cell surface in a helical pattern. This organization is thought to provide a scaffold for other biofilm-initiating components thereby contributing to cell-cell interactions (Byrd, M. S., et al., *J. Mol. Microbiol.* 2009, 73, 622-638). Psl is a polysaccharide of relatively low molecular weight (6.5 KDa) and is comprised of branched pentasaccharide repeat units (FIG. 1A) (Kocharova, N. A., et al., *J. Biol. Chem.* 1988, 263, 11291-11295).

The *Pseudomonas* Psl target can be *Pseudomonas aeruginosa* Psl, or a Psl-like oligosaccharide produced by other bacterial species, for example, *Pseudomonas fluorescens, Pseudomonas putida,* or *Pseudomonas alcaligenes.*

Monoclonal antibodies (mAbs) that specifically bind to the serotype-independent Psl exopolysaccharide were recently identified using antibody phage libraries derived from healthy individuals or patient donors in combination with functional activity screens. See Digiandomenico, A., et al., *J. Exp. Med.* 2012, 209, 1273-1287, and PCT/US2012/041538, filed Jun. 8, 2012. The anti-Psl mAbs were characterized functionally, and were shown to (a) inhibit attachment of *Pseudomonas aeruginosa* to epithelial cells, (b) promote, mediate, or enhance opsonophagocytic killing (OPK) of *P. aeruginosa,* or (c) inhibit attachment of *P. aeruginosa* to epithelial cells and promote, mediate, or enhance OPK of *P. aeruginosa.*

The antibodies were classified by competitive binding assays to bind to three different Psl epitopes, referred to as class I, II, and III (Table 1); antibodies that bound the class I and II epitopes were noncompetitive with each other, while the lone antibody targeting the class III epitope, WapR-016, partially competed with antibodies targeting the class I and II epitopes. A survey of anti-Psl mAbs binding to *P. aeruginosa* clinical isolates indicated Psl expression/accessibility among 85% of all isolates tested (147/173) with greater reactivity observed from isolates obtained from confirmed acute infections (96%). These results indicate that Psl is surface accessible and prevalent among non-mucoid and mucoid clinical isolates.

TABLE 1

Properties of anti-Psl monoclonal antibodies

| Epitope | mAb | $K_D$ (nM) | Cell attachment max. inhibition (µg/ml) | OPK $EC_{50}$ (µg/ml) |
|---|---|---|---|---|
| Class I | Cam-003 | 144 | 1.0 | 0.022 |
|  | Cam-004 | 2100 | >30.0 | 0.277 |
|  | Cam-005 | 8400 | >30.0 | >30.0 |
| Class II | WapR-001 | 0.84 | 30.0 | 0.310 |
|  | WapR-003 | 12.2 | 30.0 | 0.278 |
|  | WapR-002 | 12.6 | 30.0 | 0.396 |
| Class III | WapR-016 | 75.0 | 10.0 | 0.242 |

Class I antibodies or fragments thereof include those antibodies or antigen-binding fragments thereof that can specifically bind to the same *Pseudomonas* Psl epitope as an antibody or antigen-binding fragment thereof comprising the heavy chain variable region (VH) and light chain variable region (VL) region of WapR-004, Cam-003, Cam-004, or Cam-005, and/or can competitively inhibit *Pseudomonas* Psl binding by an antibody or antigen-binding fragment thereof comprising the VH and VL of WapR-004, Cam-003, Cam-004, or Cam-005.

Class II antibodies or fragments thereof include those antibodies or antigen-binding fragments thereof that can specifically bind to the same *Pseudomonas* Psl epitope as an antibody or antigen-binding fragment thereof comprising the heavy chain variable region (VH) and light chain variable region (VL) region of WapR-001, WapR-002, or WapR-003, and/or can competitively inhibit *Pseudomonas* Psl binding by an antibody or antigen-binding fragment thereof comprising the VH and VL of WapR-001, WapR-002, or WapR-003.

Class III antibodies or fragments thereof include those antibodies or antigen-binding fragments thereof that can specifically bind to the same *Pseudomonas* Psl epitope as an antibody or antigen-binding fragment thereof comprising the heavy chain variable region (VH) and light chain variable region (VL) region of WapR-016, and/or can competitively inhibit *Pseudomonas* Psl binding by an antibody or antigen-binding fragment thereof comprising the VH and VL of WapR-016.

Anti-Psl Mabs are described in detail in PCT/US2012/041538, filed Jun. 8, 2012, incorporated herein by reference in its entirety. The amino acid structures of the VH and VL regions of the exemplary anti-Psl Mabs characterized in Table 1 are provided in Table 2:

TABLE 2

Reference VH and VL amino acid sequences*

| Antibody Name | VH | VL |
|---|---|---|
| Cam-003 | QVRLQQSGPGLVKPSET LSLTCTVSGGSTSPYFW SWLRQPPGKGLEWIGYI HSNGGTNYNPSLKSRL TISGDTSKNQFSLNLSF VTAADTALYYCARTDY DVYGPAFDIWGQGTM VTV SEQ ID NO: 1 | SSELTQDPAVSVALGQTVRITCQGDS LRSYYASWYQQKPGQAPVLVIYGKN NRPSGIPDRFSGSSSGNTASLTITGAQ AEDEADYYCNSRDSSGNHVVFGGGT KLTVL SEQ ID NO: 2 |
| Cam-004 | QVQLQQSGPGRVKPSE TLSLTCTVSGYSVSSGY YWGWIRQSPGTGLEWI GSISHSGSTYYNPSLKS RVTISGDASKNQFFLRL TSVTAADTAVYYCARS EATANFDSWGRGTLVT VSS SEQ ID NO: 3 | SSELTQDPAVSVALGQTVRITCQGDS LRSYYASWYQQKPGQAPVLVIYGKN NRPSGIPDRFSGSSSGNTASLTITGAQ AEDEADYYCNSRDSSGNHVVFGGGT KLTVL SEQ ID NO: 2 |
| Cam-005 | QVQLQQSGPGLVKPSET LSLTCTVSGGSVSSSGY YWTWIRQPPGKGLEWI GSIYSSGSTYYSPSLKS RVTISGDTSKNQFSLKL SSVTAADTAVYYCARL NWGTVSAFDIWGRGTL VTV SEQ ID NO: 4 | SSELTQDPAVSVALGQTVRITCQGDS LRSYYASWYQQKPGQAPVLVIYGKN NRPSGIPDRFSGSSSGNTASLTITGAQ AEDEADYYCNSRDSSGNHVVFGGGT KLTVL SEQ ID NO: 2 |
| WapR-001 | EVQLLESGGGLVQPGG SLRLSCSASGFTFSRYP MHWVRQAPGKGLEYV SDIGTNGGSTNYADSV KGRFTISRDNSKNTVYL QMSSLRAEDTAVYHCV AGIAAAYGFDVWGQG TMVTVSS SEQ ID NO: 5 | QAGLTQPASVSGSPGQSITISCTGTSS DIATYNYVSWYQQHPGKAPKLMIYE GTKRPSGVSNRFSGSKSGNTASLTIS GLQAEDEADYYCSSYARSYTYVFGT GTELTVL SEQ ID NO: 6 |
| WapR-002 | QVQLVQSGGGLVQPGG SLRLSCSASGFTFSSYP MHWVRQAPGKGLDYV SDISPNGGSTNYADSV KGRFTISRDNSKNTLFL QMSSLRAEDTAVYYCV MGLVPYGFDIWGQGTI, VTVSS SEQ ID NO: 7 | QTVVTQPASVSGSPGQSITISCTGTSS DVGGYNYVSWYQQHPGKAPKLMIY EVSNRPSGVSNIIFSGSKSGNTASLTIS GLQAEDEADYYCSSYTTSSTYVFGT GTKVTVL SEQ ID NO: 8 |

TABLE 2-continued

Reference VH and VL amino acid sequences*

| Antibody Name | VH | VL |
|---|---|---|
| WapR-003 | QMQLVQSGGGLVQPGG SLRLSCSASGFTFSSYP MHWVRQAPGKGLDYV SDISPNGGATNYADSV KGRFTISRDNSKNTVYL QMSSLRAEDTAVYYCV MGLVPYGFDNWGQGT MVTVSS SEQ ID NO:9 | QTVVTQPASVSASPGQSITISCAGTSG DVGNYNFVSWYQQHPGKAPKLLIYE GSQRPSGVSNRFSGSRSGNTASLTIS GLQAEDEADYYCSSYARSYTYVFGT GTKLTVL SEQ ID NO: 10 |
| WapR-016 | EVQLVESGGGLVQPGGSL RLSCAASGYTFSSYATSWV RQAPGKGLEWVAGISGSG DTTDYVDSVKGRFTVSRD NSKNTLYLQMNSLRADDT AVYYCASRGGLGGYYRG GFDFWGQGTMVTVSS SEQ ID NO: 11 | QSVLTQPASVSGSPGQSITISCTGTSSDVG GYNYVSWYQQHPGKAPKLMIYEVSNRPS GVSNRFSGSKSGNTASLTISGLQAEDEAD YCSSYSSGTVVFGGGTELTVL SEQ ID NO: 12 |

*VH and VL CDR1, CDR2, and CDR3 amino acid sequences are underlined

III. Synthetic Oligosaccharide Subunits

This disclosure provides synthetic oligosaccharide subunits of a *Pseudomonas* Psl oligosaccharide, e.g., a *Pseudomonas aeruginosa* Psl oligosaccharide. Since little is known about Psl biosynthesis and how this complex carbohydrate is assembled on the surface of *P. aeruginosa*, chemically synthesized oligosaccharides were prepared to accurately define the binding requirements of the anti-Psl mAbs. The disclosure provides chemical synthesis and characterization of a panel of oligosaccharides modelled on the reported structure of Psl (FIG. 1A) and define the ability of anti-Psl mAbs to react with each compound. Target compound 1 (FIG. 1B, compound 1) is a decasaccharide composed of two repeating units. This compound contains all possible substructures of the repeating Psl polysaccharide. Target compound 2 (FIG. 1B, compound 2) is a pentasaccharide, and represents a single repeating unit. Target compound 3 (FIG. 1B, compound 3) is a hexasaccharide comprising the repeating unit having an additional distal glucoside. Finally, target compound 4 (FIG. 1B, compound 4) is a tetrasaccharide lacking the branching mannoside of the repeating pentasaccharide unit. As described in the Examples below, binding studies confirmed that anti-Psl mAbs targeting the class II and class III epitopes bound synthetic Psl oligosaccharides. Interestingly, anti-Psl mAbs targeting the class I epitope, which yield the most protective functional activities against *P. aeruginosa*, were incapable of binding synthetic compounds suggesting additional yet to be elucidated modifications to the reported Psl structure.

A synthetic oligosaccharide subunit defining the class III epitope of the *Pseudomonas aeruginosa* Psl oligosaccharide is provided as a synthetic oligosaccharide subunit comprising the trisaccharide of formula I.

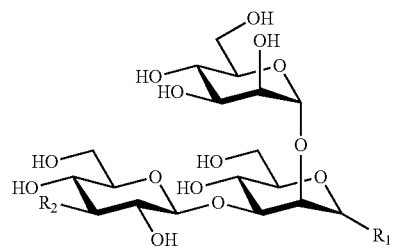

In certain aspects, $R_1$ can be a hydroxyl group (—OH) or a trisaccharide subunit according to the following formula.

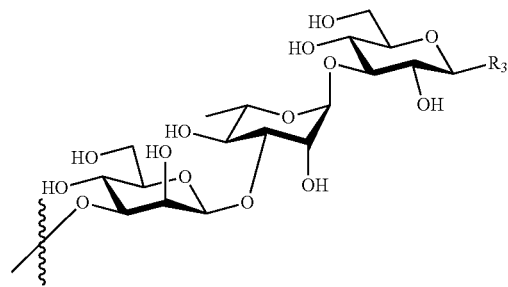

In certain aspects, $R_2$ can be a hydroxyl group (—OH) or a tetrasaccharide subunit according to the following formula.

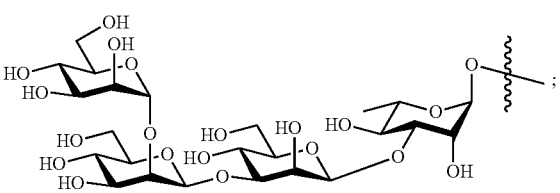

In certain aspects, $R_3$ can be —OX, where X is hydrogen, an alkyl group or an aryl group, a linker including, without limitation, —O—$(CH_2)_n$—$NH_2$, —O—$(CH_2)_n$—COOH, —O—$(CH_2)_n$—$N_3$, —O—$(CH_2)_n$—$S(CH_2)_m$—$NH_2$, —O—$(CH_2)_n$—$S(CH_2)_m$—COOH, —O—$(CH_2)_n$—$S(CH_2)_m$—N, —O—$(CH_2)_n$—$SO_2(CH_2)_m$—$NH_2$, —O—$(CH_2)_n$—$SO_2(CH_2)_m$—COOH, or —O—$(CH_2)_n$—$SO_2(CH_2)_m$—$N_3$, where n and m are the same or different and are independently 0, 1, 2, 3, 4, 5, 6, 7, 8, 9, or 10, or a linker coupled to a heterologous moiety via conjugation, where the heterologous moiety can be, for example, a protein, a lipid or a polymer as noted above. Other suitable linkers and conjugated moieties, as well as methods for conjugating oligosaccharides at the anomeric carbon, are well known to those of ordinary skill in the art. See, e.g., Hevey, Rand Ling, C.-C., 2012, *Future Med. Chem.* 4:545-584; Morelli, L., et al., 2011, *Eur. J. Org. Chem.* 29:5723-5777; and Costantino, P., et al., 2011, *Exp. Opin. Drug. Disc.* 6:1045-1066, each of which is incorporated herein by reference in its entirety.

In certain aspects the synthetic oligosaccharide subunit defining the class III epitope of the *Pseudomonas aeruginosa* Psl oligosaccharide comprises the hexasaccharide shown as compound 4 in FIG. 1B, or the decasaccharide shown as compound 1 in FIG. 1B.

The synthetic oligosaccharide subunit as described above can be specifically bound by class HIII anti-Psl antibodies, or antigen-binding fragments thereof. For example, the synthetic oligosaccharide subunit can be specifically bound by the anti-Psl monoclonal antibody WapR-016, or an antigen binding fragment thereof, which comprises VH and VL amino acid sequences of SEQ ID NO:11 and SEQ ID NO:12, respectively. As would be understood by persons of ordinary skill in the art, the synthetic oligosaccharide subunit described above can also be bound by anti-Psl antibodies which bind to the same epitope as WapR-016. As described in more detail in the Examples, class III anti-Psl antibodies do not bind to the tetrasaccharide shown as f 3 in FIG. 1B, or to the pentasaccharide shown as compound 2 in FIG. 1B.

A synthetic oligosaccharide subunit defining the class II epitope of the *Pseudomonas aeruginosa* Psl oligosaccharide is provided as a synthetic oligosaccharide subunit comprising the tetrasaccharide of formula II.

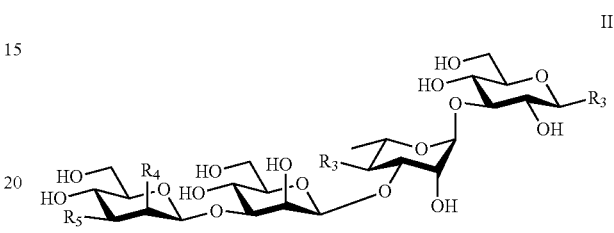

II

In certain aspects, $R_4$ can be a hydroxyl group (—OH) or a monosaccharide subunit according to the following formula.

In certain aspects, $R_5$ can be a hydroxyl group (—OH) or a pentasaccharide subunit according to the following formula:

or a monosaccharide subunit according to the following formula.

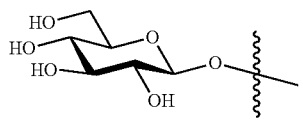

In certain aspects, $R_3$ can be —OX, where X is hydrogen, an alkyl group or an aryl group, a linker including, without limitation, —O—$(CH_2)_n$—$NH_2$, —O—$(CH_2)_n$—COOH, —O—$(CH_2)_n$—N, —O—$(CH_2)_n$—$S(CH_2)_m$—$NH_2$, —O—$(CH_2)_n$—$S(CH_2)_m$—COOH, —O—$(CH_2)_n$—$S(CH_2)_m$—$N_3$, —O—$(CH_2)_n$—$SO_2(CH_2)_m$—$NH_2$, —O—$(CH_2)_n$—$SO_2(CH_2)_m$—COOH, or —O—$(CH_2)_n$—$SO_2(CH_2)_m$—$N_3$, where n and m are the same or different and are independently 0, 1, 2, 3, 4, 5, 6, 7, 8, 9, or 10, or a linker coupled to a heterologous moiety via conjugation, where the heterologous moiety can be, for example, a protein, a lipid or a polymer as noted above.

In certain aspects the synthetic oligosaccharide subunit defining the class II epitope of the *Pseudomonas aeruginosa* Psl oligosaccharide comprises the hexasaccharide shown as compound 4 in FIG. 1B, or the decasaccharide shown as compound 1 in FIG. 1B, the tetrasaccharide shown as compound 3 in FIG. 1B, or the pentasaccharide shown as compound 2 in FIG. 1B.

The synthetic oligosaccharide subunit as described above can be specifically bound by class II anti-Psl antibodies, or antigen-binding fragments thereof. For example, the synthetic oligosaccharide subunit can be specifically bound by the anti-Psl monoclonal antibody WapR-001, or an antigen binding fragment thereof, which comprises VH and VL amino acid sequences of SEQ ID NO:5 and SEQ ID NO:6, respectively, the anti-Psl monoclonal antibody WapR-002, or an antigen binding fragment thereof, which comprises VH and VL amino acid sequences of SEQ ID NO:7 and SEQ ID NO:8, respectively, or the anti-Psl monoclonal antibody WapR-003, or an antigen binding fragment thereof, which comprises VH and VL amino acid sequences of SEQ ID NO:9 and SEQ ID NO: 10, respectively. As would be understood by persons of ordinary skill in the art, the synthetic oligosaccharide subunit described above can also be bound by anti-Psl antibodies which bind to the same epitope as WapR-001, WapR-002, and WapR-003.

In certain aspects, the disclosure provides synthetic intermediates of the synthetic oligosaccharide subunits described above. Non-limiting examples of intermediates are presented in FIG. 2 and in Example 2.

IV. Oligosaccharide Conjugates

In certain aspects, a synthetic oligosaccharide subunit as provided herein can be attached to a heterologous molecule, e.g., a polypeptide, a lipid or a polymer. In certain aspects the oligosaccharide subunit is covalently attached to the heterologous molecule, e.g., conjugated thereto. Oligosaccharides are typically conjugated to heterologous molecules through a linker, an inter-glycosidic oxygen or sulphur.

An oligosaccharide subunit as provided herein can be attached though a linker to a protein carrier using conventional chemical techniques providing for linkage of the oligosaccharide to the carrier. Methods to effect covalent linkages between a linker and both a protein carrier and the oligosaccharide are well known in the art. Non-limiting examples can involve the use of complementary functional groups on the hetero- or homo-bifunctional cross-coupling reagent. In certain aspects, the complementary functional groups are selected relative to the functional groups available on the oligosaccharide or protein carrier for bonding or which can be introduced onto the oligosaccharide or carrier for bonding. For example, reaction between a carboxylic acid of either a linker or a protein and a primary or secondary amine of the protein or the linker in the presence of suitable, well-known activating agents results in formation of an amide bond; reaction between an amine group of either the linker or the protein and a sulfonyl halide of the protein or the linker results in formation of a sulfonamide bond covalently; and reaction between an alcohol or phenol group of either the linker or the protein carrier and an alkyl or aryl halide of the carrier or the linker results in formation of an ether bond covalently linking the carrier to the linker. Similarly these complementary reactions can occur between the linker and the oligosaccharide to form a linkage between the oligosaccharide and the linker.

Non-limiting examples of proteins to which an oligosaccharide subunit as provided herein can be conjugated include albumin, e.g., human serum albumin or bovine serum albumin, tetanus toxoid, an immunoglobulin Fc region, or keyhole limpet hemocyanin.

Non-limiting examples of lipids to which an oligosaccharide subunit as provided herein can be conjugated include fatty acid lipophilic chains include $C_6$-$C_{24}$ fatty acids, saturated fatty acids such as lauric, myristic, palmitic, stearic, arachidic, behenic, and lignoceric acids; and unsaturated fatty acids, such as palmitoleic, oleic, linoleic, linolenic and arachidonic acids.

Non-limiting examples of polymers to which an oligosaccharide subunit as provided herein can be conjugated include polyalkylene glycol chains, e.g., polyethylene glycol. Useful polyethylene glycols have the formula H—(O—$CH_2$—$CH_2)_n$OH, where n, the number of ethylene oxide units, is from 4 to 14. Useful polyethylene glycol fatty alcohol ethers include those wherein the ethylene oxide units (n) are between 1 to 8, and the alkyl group is from $C_6$ to $C_{18}$.

VII. Identification and Epitope Mapping of Anti-Psl Antibodies

In certain aspects, the disclosure provides a method of evaluating the binding characteristics of one or more anti-*Pseudomonas aeruginosa* Psl antibodies or antigen-binding fragments thereof to *Pseudomonas aeruginosa* Psl epitope. Antibodies or fragments thereof to be evaluated can include antibodies already identified to bind to Psl, antibodies or fragments thereof already identified to bind to *P. aeruginosa*, or even random antibody libraries, or antibody libraries prepared from convalescent or recovered individuals who were at one time infected with *P. aeruginosa*.

The method can include (a) contacting one or more antibodies or fragments thereof with one or more oligosaccharide subunits provided herein under conditions that allow the antibody to bind an oligosaccharide subunit; and (b) detecting the presence of a complex of an antibody or fragment thereof and an oligosaccharide subunit. Detection can be through any suitable immunoassay, many of which are known to those of ordinary skill in the art. In certain aspects the immunoassay is an ELISA assay. According to this method one or more antibodies can be classified as binding to a class 11 epitope if they bind to each of the tetrasaccharide, pentasaccharide, hexasaccharide, and decasaccharide Psl oligosaccharide subunit compounds provided herein, e.g., the compounds 1, 2, 3, and 4 shown in FIG. 1B. Alternatively one or more antibodies can be classified as binding to a class III epitope if they bind to the hexasaccharide and/or decasaccharide Psl oligosaccharide subunit compounds provided herein, e.g., compounds 1 and 4 in FIG. 1B, but do not bind to the tetrasaccharide or the pentasaccharide Psl oligosaccharide subunit compounds provided herein, e.g., compounds 2 and 3 in FIG. 1B.

In certain aspects this method can be used to select for improved anti-Psl antibodies, e.g., exhibiting greater affinity or avidity for Psl.

In another aspect, the method can be used for screening for antibodies which bind to *Pseudomonas aeruginosa* Psl. The method can include: (a) contacting an antibody or antibody fragment library with one or more of the oligosaccharide subunits provided herein under conditions that allow Psl-specific antibodies or fragments thereof to bind one or more of the oligosaccharide subunits, while antibodies not specific for Psl do not bind; (b) detecting the presence of a complex of an antibody or fragment thereof and an oligosaccharide subunit; and (c) selecting antibodies which bind to the oligosaccharide subunit.

Antibody libraries, such as phage display libraries, are well-known in the art. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with scFv, Fab, Fv OE DAB (individual Fv region from light or heavy chains) or disulfide stabilized Fv antibody domains recombinantly fused to either the phage gene III or gene VII protein. Exemplary methods are set forth, for example, in EP 368 684 B1; U.S. Pat. No. 5,969,108, Hoogenboom, H. R. and Chames, *Immunol. Today* 21:371 (2000); Nagy et al. *Nat. Med.* 8:801 (2002); Huie et al., *Proc. Natl. Acad. Sci. USA* 98:2682 (2001); Lui et al., *J. Mol. Biol.* 315:1063 (2002), each of which is incorporated herein by reference. Several publications (e.g., Marks et al., *Bio/Technology* 10:779-783 (1992)) have described the production of high affinity human antibodies by chain shuffling, as well as combinatorial infection and in vivo recombination as a strategy for constructing large phage libraries. In another embodiment, Ribosomal display can be used to replace bacteriophage as the display platform (see, e.g., Hanes et al., *Nat. Biotechnol.* 18:1287 (2000); Wilson et al., *Proc. Natl. Acad. Sci. USA* 98:3750 (2001); or Irving et al., *J. Immunol. Methods* 248:31 (2001)). In yet another embodiment, cell surface libraries can be screened for antibodies (Boder et al., *Proc. Natl. Acad. Sci. USA* 97:10701 (2000); Daugherty et al., *J. Immunol. Methods* 243:211 (2000)). Such procedures provide alternatives to traditional hybridoma techniques for the isolation and subsequent cloning of monoclonal antibodies.

VIII. Pharmaceutical Compositions Comprising Synthetic Oligosaccharide Subunits of *P. aeruginosa* Psl In certain aspects, the synthetic oligosaccharide subunits of Psl can be immunogenic compositions for inducing immune responses, such as vaccine compositions. In certain aspects protein conjugates comprising the synthetic oligosaccharide subunits, can be used as vaccines for treating *Pseudomonas* infections.

As used herein, the terms "treatment", "treating", and the like, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease. "Treatment", as used herein, includes, but is not limited to: (a) preventing *Pseudomonas*-related disease or condition from occurring in a subject which may be predisposed to the disease, or which may be susceptible to the disease, but has not yet been diagnosed as having it (e.g., where the subject is susceptible to infection by *Pseudomonas*, but has not yet been infected), including, but not limited to, reducing the risk of disease and/or death following infection by *Pseudomonas*; reducing the incidence of disease and/or death following infection by *Pseudomonas*; reducing the incidence or risk of infection by *Pseudomonas*; and reducing the extent of disease following infection by *Pseudomonas*; (b) inhibiting a disease or symptoms resulting from *Pseudomonas* infection, e.g., arresting its development, slowing its progression; or (c) relieving a disease or symptoms resulting *Pseudomonas* infection, e.g., causing regression of the disease or symptoms.

Glycoconjugate vaccines are among the safest and most efficacious vaccines developed to date and are widely used for the prevention of life threatening bacterial infections such as meningitis and pneumonia (Costantino, P., et al., *Expert Opin. Drug Discov.* 2011, 6, 1045-1066). The identification of mAbs that bind unique epitopes of bacterial polysaccharide and elicit different functional activities highlights the importance of synthetic chemistry in epitope mapping and could have important implications for the development of future glycoconjugate vaccines. In particular, careful selection of a carbohydrate epitope of a bacterial polysaccharide can be critical for eliciting optimal protective responses. For example, the observation that WapR-016 reacts potently to the hexasaccharide containing a terminal glucoside but poorly to a compound harboring a similar embedded glucoside (see Example 2, below) magnifies the importance of appropriate synthetic vaccine design for eliciting relevant antibodies.

Accordingly in one aspect this disclosure provides a method for treating a *Pseudomonas* infection in a subject, comprising administering to a subject in need of treatment a composition comprising a synthetic oligosaccharide subunit of *P. aeruginosa* Psl as described herein. In certain aspects, the oligosaccharide subunit is conjugated to a carrier, e.g., a protein such as human or bovine serum albumin, tetanus toxoid, or the like, a lipid, or a polymer. An effective amount is sufficient to effect treatment, as defined above. The effective amount and method of administration of a particular therapeutic or prophylactic treatment can vary based on the individual patient and the stage of the disease, as well as other factors known to those of skill in the art.

A composition comprising a synthetic oligosaccharide subunit of *P. aeruginosa* Psl used in this disclosure can include pharmaceutically acceptable carriers well known to those of ordinary skill in the art. Preparations for parenteral administration include sterile aqueous or non-aqueous solutions, suspensions, and emulsions. Certain pharmaceutical compositions as disclosed herein can be orally administered in an acceptable dosage form including, e.g., capsules, tablets, aqueous suspensions or solutions. Certain pharmaceutical compositions also can be administered by nasal aerosol or inhalation. Preservatives and other additives can also be present such as for example, antimicrobials, antioxidants, chelating agents, and inert gases and the like. Suitable formulations for use in the therapeutic methods disclosed herein are described in Remington's Pharmaceutical Sciences, Mack Publishing Co., 16th ed. (1980).

EXAMPLES

Example 1: Synthesis of Oligosaccharide Subunits of *Pseudomonas aeruginosa* Psl for Epitope Mapping Reagents and General Procedures.

Reagents were obtained from commercial sources and used as purchased. Dichloromethane (DCM) was freshly distilled using standard procedures. Other organic solvents were purchased anhydrous and used without further purification. Unless otherwise noted, all reactions were carried out at room temperature in oven-dried glassware with magnetic stirring. Molecular sieves were flame dried under high vacuum prior to use. Organic solutions were concentrated under diminished pressure with bath temperatures <40° C. Flash column chromatography was carried out on silica gel G60 (Silicycle, 60-200 μm, 60 Å). Thin-layer chromatography (TLC) was carried out on Silica gel 60 $F_{254}$ (EMD Chemicals Inc.) with detection by UV absorption (254 nm) where applicable, by spraying with 20% sulfuric acid in ethanol followed by charring at ~150° C., or by spraying with a solution of $(NH_4)_6Mo_7O_{24} \cdot H_2O$ (25 g/L) in 10% sulfuric acid in ethanol followed by charring at ~150° C. $^1H$ and $^{13}C$ NMR spectra were recorded on a Varian Inova-300 (300175 MHz), a Varian Inova-500 (500/125 MHz) a Varian Inova-600 (600/150 MHz), a Varian Inova-800 (800/200 MHz), and a Varian Inova-900 (900/225 MHz) spectrometer equipped with sun workstations. Multiplicities are quoted as singlet (s), broad singlet (br s), doublet (d), doublet of doublets (dd), triplet (t), or multiplet (m). Spectra were assigned using COSY and HSQC experiments. Signals marked with a superscript Roman numeral I were the reducing end, whereas II and III were the second sugar from the reducing end and the non-reducing end, respectively. All chemical shifts are quoted on the δ-scale in parts per million (ppm). Residual solvent signals were used as an internal reference. Reverse-Phase HPLC was performed on an Aglient 1200 series system equipped with an auto-sampler, fraction-collector, UV-detector, and eclipse XDB-C18 column (5 μm, 4.6×250 mm or 9.4×250 mm) at a flow rate of 1.5 mL/min. Mass spectra were recorded on an Applied Biosystems 5800 MALDI-TOF proteomics analyzer. The matrix used was 2,5-dihydroxybenzoic acid (DHB) and ultamark 1621 was the internal standard.

General Procedure for Global Deprotection.

Freshly prepared NaOMe (pH 10) was added to a solution of compounds 26 (Scheme 3), 19 (Scheme 1), 20 (Scheme 1), or 6 (FIG. 2) in MeOH/DCM (2/1, v/v, at a concentration of 2 μmol oligosaccharide per mL). The reaction mixture was stirred at mom temperature overnight, and then neutralized by the addition of 10% AcOH in MeOH. The suspension was washed with DCM. The reaction mixture was diluted with DCM and washed with saturated $NaHCO_3$ and brine (30 mL). The organic layer was dried ($MgSO_4$), filtered, and the filtrate was concentrated under reduced pressure. Purification of by flash chromatography over silica gel (Hexanes/EtOAc, 1/2, v/v) gave the deacylated product. The resulting partially deprotected compound was dissolved in a mixture of t-BuOH and water (1/1, v/v, at a concentration of 2 μmol saccharide per mL) and $Pd(OH)_2/C$ (20 wt. %, Degussa type) was added. The resulting mixture was placed under a hydrogen atmosphere (1 psi). After stirring for 48 h, the catalyst was filtered off and washed thoroughly with water. The combined filtrates were concentrated under reduced pressure and the crude product was purified by BioGel P2.

Oligosaccharide Synthesis.

Oligosaccharide subunits of formulae 1-4 as shown in FIG. 1B were prepared using the building blocks shown in FIG. 2, using syntheses as shown in Schemes 1, 2, and 3, below. The assembly of oligosaccharides composed of two or more repeating units was performed by block synthesis in which a common saccharide moiety representing a full repeating unit was converted into a glycosyl donor and acceptor which was coupled to give a targeted compound (Boltje, T. J., et al., *Nat. Chem.* 2009, 1, 611-622). The building blocks for the syntheses are shown in FIG. 2.

General Considerations.

In the case of compound 1 in FIG. 1B, however, it was thought that such a strategy could be problematic because the C-3 hydroxyl of the required mannosyl acceptor was of low reactivity due to the neighboring α-mannoside at C-2 and the β-anomeric configuration of the anomeric center, which places the C-1 C-2, C-3 substituents in a crowding 1,2,3-cis configuration. Therefore, an alternative strategy was used in which tetrasaccharide donor 5 (FIG. 2) was coupled with hexasaccharide acceptor 6 (FIG. 2) to give a decasaccharide, which after global deprotection, would provide target compound 1 (FIG. 1B). Furthermore, it was envisaged that trisaccharide 15 would be an appropriate precursor for the preparation of tetrasaccharide 5 and hexasaccharide 6 thereby minimizing the required number of synthetic steps (Scheme 1).

The installation of β-mannosides was a challenging aspect of the preparation of the key building blocks 5 and 6 (FIG. 2). These 1,2-cis glycosides were difficult to introduce due to the axial C-2 substituent, which sterically blocks incoming nucleophiles from the β-face and the Δ-anomeric effect, which provides additional stabilization of the α-anomer (Gridley, J. J., et al., Chem. Soc.-Perkin Trans. 1 2000, 2000, 1471-1491; Cai, F., et al., *Adv. Carbohydr. Chem. Biochem.* 2009, 62, 251-309). A method for the construction of β-mannosidic linkages is based on work by Crich and co-workers and involves the in-situ formation of an α-anomeric triflate, which is selectively formed due to a strong endo-anomeric effect that in an $S_N2$ like-manner can be displaced by a sugar hydroxyl to give a β-mannoside (Crich, D., and Sun, S. X., *J. Am. Chem. Soc.* 1997, 119, 11217-11223; Crich, D., and Sun, S. X., *Tetrahedron* 1998, 54, 8321-8348). A prerequisite of β-mannoside formation is that the glycosyl donor is protected by a 4,6-O-benzylidene acetal. It has been proposed that this protecting group opposes oxacarbenium formation ($S_N1$ glycosylation) due to the torsional strain engendered by the half chair or boat conformation of this intermediate. In addition, the 4,6-O-acetal forces the O-6 substituent in a tg conformation, which places its dipole anti-parallel to the electron deficient anomeric center formed in the transition state, thereby causing a destabilizing effect (Jensen, H. H. et al., *J. Am. Chen. Soc.* 2004, 126, 9205-9213).

Preparation of the Building Blocks of FIG. 2.

It was envisaged that monosaccharides 7-12 would be well suited for the preparation of the key building blocks 5 and 6 (FIG. 2). These derivatives were modified by the temporary protecting groups t-butyldimethylsilyl (TBS) and 2-methylnaphthyl (Nap), which can be removed in a sequential manner allowing extension of the growing oligosaccharide chain and installation of the branching moieties. Furthermore, a 4,6-O-benzylidene protected mannosyl donor modified by a C-2 silyl ether and a C-3 Nap ether provided optimal β-anomeric selectivity (Boltje, T. J., et al., *Org. Lett.* 2010, 12, 4636-4639). Thus, mannosyl donors 7 and 8 were employed for the installation of the β-mannosides. Furthermore, mannosyl donor 9 (Waschke, D., et al., *Org. Lett.* 2011, 13, 3628-3631) which was modified by an acetyl ester at C-2 t perform neighboring group participation during the glycosylation, was expected to be ideally suited for the preparation of the branching α-mannosides. Rhamnnosyl acceptor 10 (Marino-Albernas, J. R., et al., *Carbohydr. Res.* 1993, 245, 245-257) has a C-3 hydroxyl, which after β-mannosylation, will give a product with an anomeric allyl ether that can be removed and converted into a trichloroacetimidate leaving group for further glycosylation (Schmidt, R. R. and Kinzy, W., *Adv. Carbohydr. Chem. Biochem.* 1994, 50, 21-123; Zhu, X. M., and Schmidt, R. R., *Angew. Chem., Int. Ed.* 2009, 48, 1900-1934). Finally, glucosyl donor 11 was the precursor for the preparation of building block 12, which is modified by an azidopropyl spacer that offers opportunities for conjugation to carrier proteins. Glycosyl donor 11 was also employed for the installation of the backbone β-glucoside.

Synthesis of the hexasaccharide subunit (formula 4 in FIG. 1B) was performed as shown in Scheme 1:

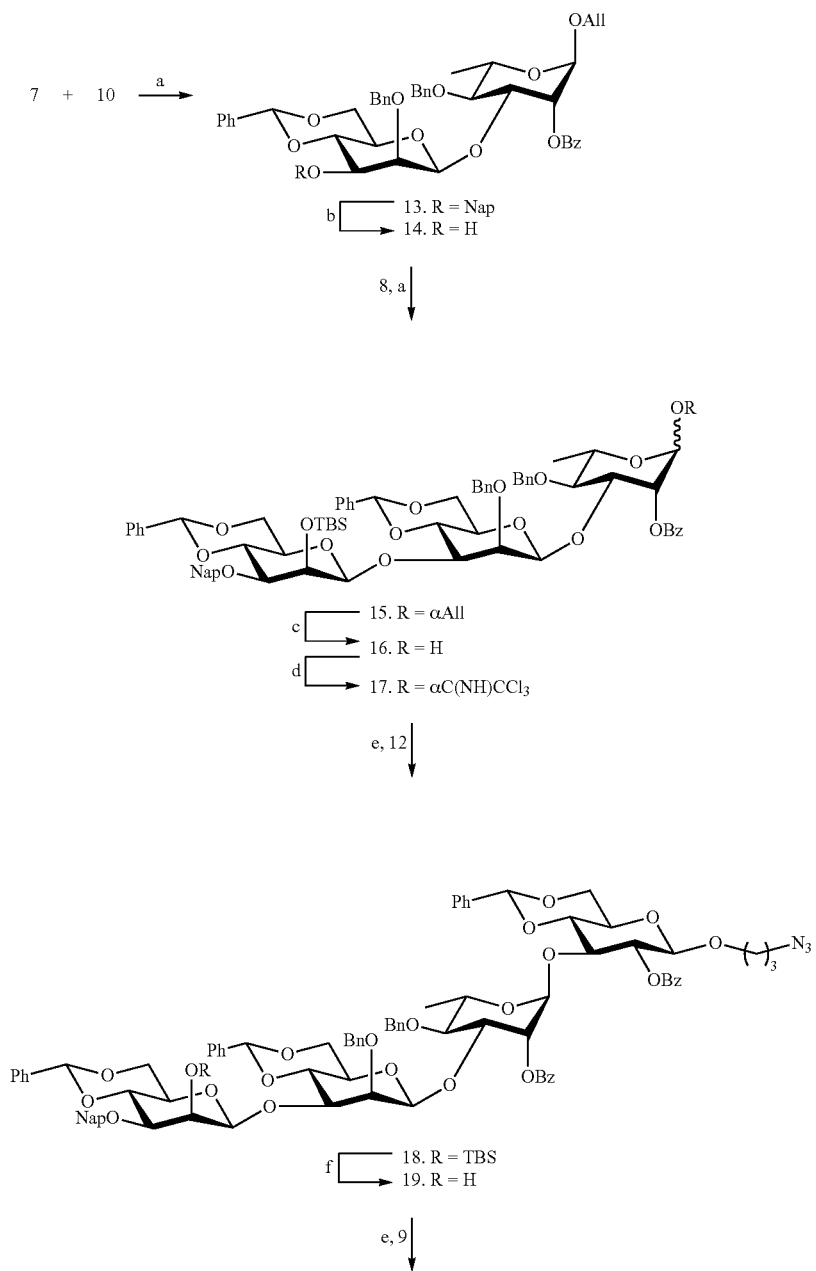

-continued

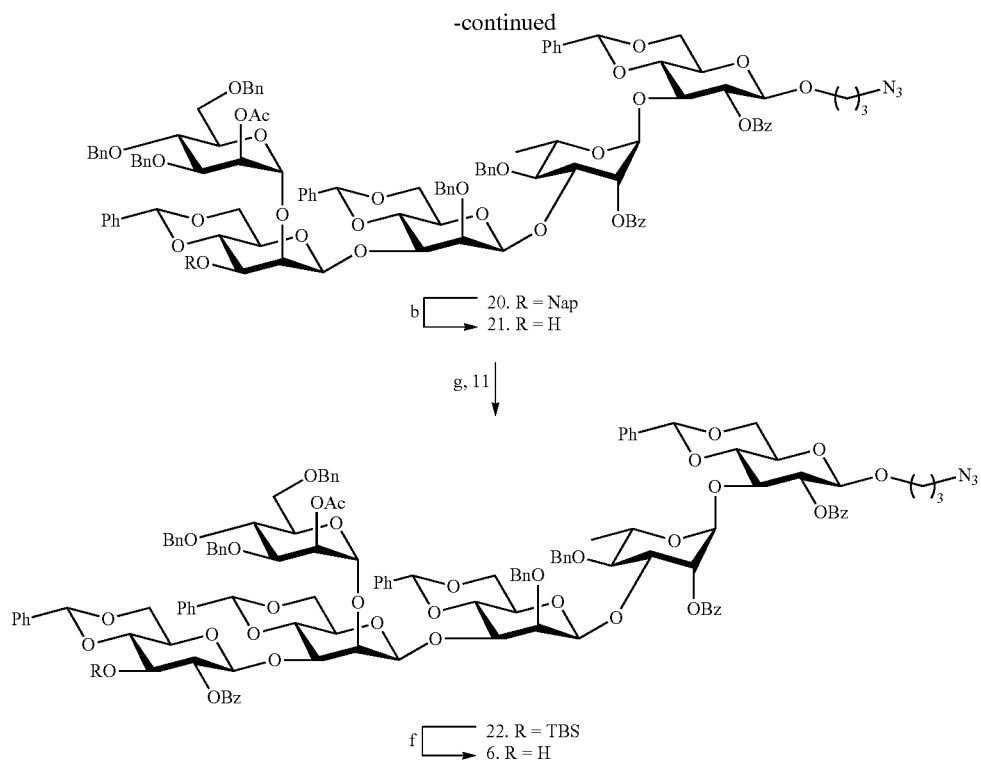

b ⎡ 20. R = Nap
  ⎣→ 21. R = H g, 11 ↓ f ⎡ 22. R = TBS
  ⎣→ 6. R = H

Reagents and conditions. (a) BSP, DTBMP, Tf$_2$O, DCM, -60° C. (75% for 13, α/β = 1/12, 72% for 15, α/β = 1/10); (b) DDQ, DCM/H$_2$O (92% for 14, 81% for 21); (c) (Ph$_3$P)$_3$RhCl, DIPEA, toluene, Δ then HgO, HgCl$_2$, acetone/H$_2$O (80%, 2 steps); (d) CCl$_3$CN, Cs$_2$CO$_3$, DCM (85%); (e) TMSOTf, DCM, -30° C. (70% for 18, 82% for 20); (f) HF pyridine (90% for 19, 85% for 6); (g) NIS, TMSOTf, DCM, 0° C. (68%).

Hexasaccharide 6, contains two β-mannosides and has a crowded 1,2,3-cis arrangement of glycosides (Scheme 1). Thus, pre-activation of thiomannosyl donor 7 with 1-benzenesulfinylpiperidine (BSP) and triflic anhydride (Tf$_2$O) (Codee, J. D. C., et al., *Org. Lett.* 2003, 5, 1519-1522) at −60° C. followed by the addition of acceptor 10 (Marino-Albernas, J. R., et al., *Carbohydr. Res.* 1993, 245, 245-257) afforded disaccharide 13 in an excellent yield of 75% as mainly the β-anomer (α/β=1/12) (Scheme 1). The small amount of unwanted α-anomer could easily be removed by silica gel column chromatography. Oxidative removal of the Nap ether of 13 using excess 2,3-dichloro-5,6-dicyano-1,4-benzoquinone (DDQ) (Gaunt, M. J. et al., *J. Org. Chem.* 1998, 63, 4172-4173; Xia, J., et al., *Tetrahedron Lett.* 2000, 41, 169-173) provided the corresponding disaccharide acceptor 14. Pre-activation of thiomannoside 8 with p-nitrophenylsulfenyl chloride (p-NO$_2$CH$_4$SCl) and silver triflate (Crich, D., et al., *Carbohydr. Res.* 2008, 343, 1858-1862) in the presence of DTBMP at −78° C. followed by the addition of acceptor 14 did not afford the desired product. Therefore, BSP and Tf$_2$O was employed as the activator system, which gave trisaccharide 15 as mainly the β-anomer in a yield of 72% (α/β=1/10). Next, the anomeric allyl ether of 15 was removed by treatment with PdCl$_2$ to give hemiacetal 16, but with a yield of only 40% due to unexpected oxidation of the allyl ether to a propene-2-one ether. (Li, Z. J., et al., *Carbohydr. Res.* 1999, 317, 191-192). This problem was avoided by a two-step process involving isomerization of the terminal alkene using Wilkinson's catalyst and DIPEA in refluxing toluene to give an intermediate enol ether, which was cleaved by the treatment with mercuric(II) oxide and mercuric(II) chloride in acetone/water to give 16 in a yield of 80% over two steps. Lactol 16 was converted into the corresponding trichloroacetimidate 17 by reaction with trichloroacetonitrile in the presence of Cs$_2$CO$_3$ and a TMSOTf-catalyzed glycosylation ((Schmidt, R. R. and Kinzy, W., *Adv. Carbohydr. Chem. Biochem.* 1994, 50, 21-123; Zhu, X. M., and Schmidt, R. R., *Angew. Chem., Int. Ed.* 2009, 48, 1900-1934) of 17 with glucosyl acceptor 12 furnished tetrasaccharide 18 in a yield of 70% as only the α-anomer due to neighboring group participation of the C-2 benzoate ester. Removal of the TBS ether of 18 by treatment with excess HF in pyridine proceeded smoothly without affection any of the other protecting groups to give glycosyl acceptor 19. A TMSOTf promoted glycosylation of mannosyl donor 9 (Waschke, D., et al., *Org. Lett.* 2011, 13, 3628-3631) with tetrasaccharide acceptor 19 in DCM provided pentasaccharide 20 in a yield of 82%. The use of the more readily accessible donor phenyl 2,3,4,6-tetra-O-benzyl-1-thio-α-D-mannopyranoside in combination with NIS/TMSOTf as the activator in diethyl ether as the solvent led to a low yield of coupling product. Removal of the Nap ether of 20 using standard conditions followed by glycosylation of the resulting acceptor 21 with glucosyl donor 11 using NIS/TMSOTf as the activator provided hexasaccharide 22 in a yield of 68%. Finally, HF-pyridine mediated removal of the TBS ether of 22 gave the target hexasaccharide acceptor 6 in good yield. The orthogonality of the TBS and Nap groups would have made it possible to first install the 0-glucoside and then the α-mannoside. However, such a strategy was expected to be less productive because it requires a glycosylation of a C-2 hydroxyl flanked by 1,2-cis glycosides. Finally, hexasaccharide acceptor 6 was subjected to global deprotection as described above to produce formula 4 in FIG. 1B.

Synthesis of the tetrasaccharide subunit (formula 3 in FIG. 1B) was performed as follows. Formula 19 (Scheme 1) was subjected to global deprotection as described above to produce formula 3 in FIG. 1B.

Synthesis of the pentasaccharide subunit (formula 2 in FIG. 1B) was performed as follows. Formula 20 (Scheme 1) was subjected to global deprotection as described above to produce formula 2 in FIG. 1B.

Synthesis of the decasaccharide subunit (formula 4 in FIG. 1B) was performed as shown in Schemes 2 and 3:

Scheme 2

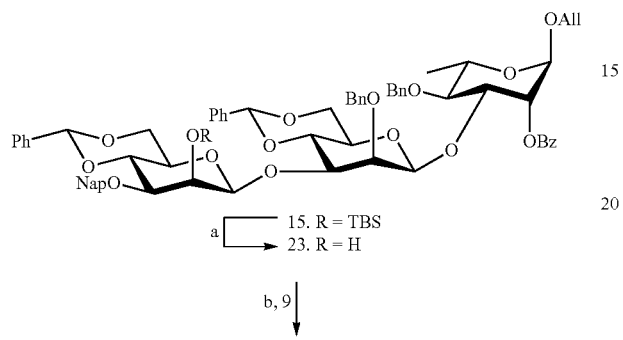

15. R = TBS
23. R = H a b, 9

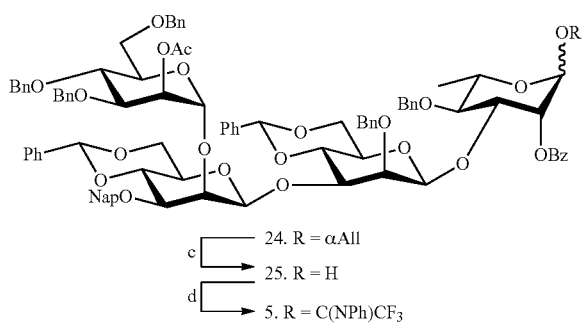

24. R = αAll
25. R = H
5. R = C(NPh)CF$_3$ c d

Reagents and Conditions. (a) HF, pyridine (86%); (b) TMSOTf, DCM, -30° C. (70%); (c) (Ph$_3$P)$_3$RhCl, DIPEA, toluene, Δ then HgO, HgCl$_2$, acetone/H$_2$O (76%, 2 steps); (d) 2,2,2-trifluoro-N-phenylacetimidoyl chloride, DBU, DCM (90%).

Scheme 3

5 + 6 a

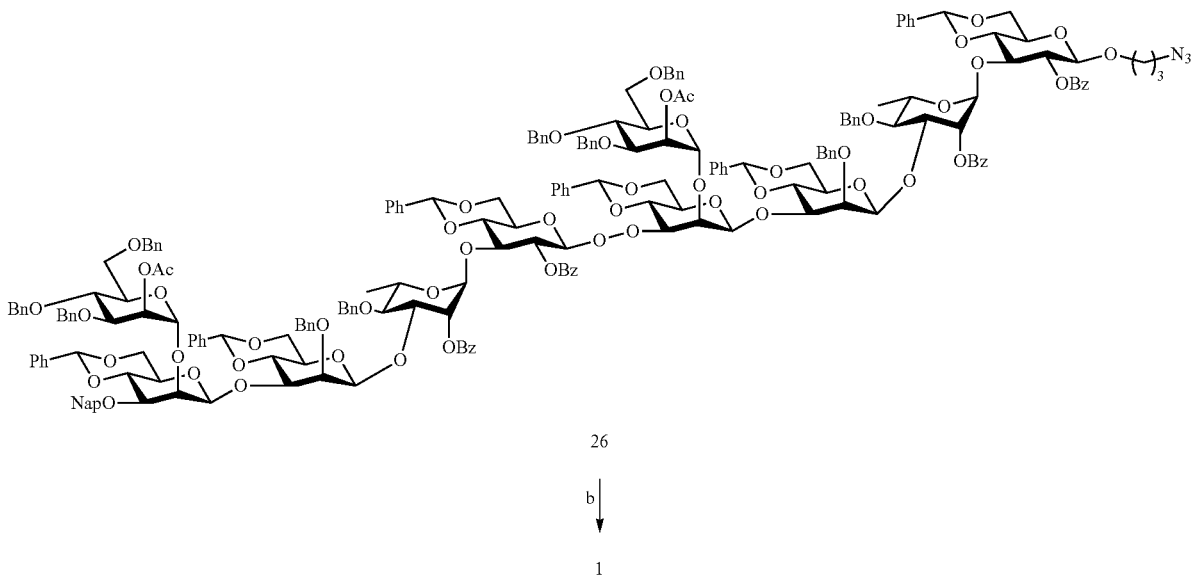

26 b

1

Reagents and conditions. (a) TMSOTf, DCM, -30° C. (70%); (b) NaOMe/MeOH, MeOH, DCM then H$_2$, Pd(OH)$_2$/C, $^t$BuOH/H$_2$O (70%, 2 steps).

Tetrasaccharide donor 5 was prepared starting from common trisaccharide 15. Thus, the TBS group of 15 was removed by treatment with HF pyridine and the resulting acceptor 23 was coupled with mannosyl donor 9 to provide tetrasaccharide 24. The latter compound was converted into glycosyl donor 5 by removal of the anomeric allyl ether using the two-step procedure to give 25 followed by treatment with 2,2,2-trifluoro-N-phenylacetimidoyl chloride in the presence of 1,8-diazabicyclo[5.4.0]undec-7-ene.

The coupling of 5 with 6 in the presence of TMSOTf in DCM at 0° C. gave decasaccharide 26 in a yield of 70% as only the β-anomer due to neighboring group participation of the C-2 ester of the glycosyl donor (Scheme 3). The deprotection of 26 was easily accomplished by a two-step procedure to furnish decasaccharide 1 as described above, and involved the removal of the ester protecting groups by treatment with sodium methoxide in methanol followed by hydrogenation over $Pd(OH)_2$/C in a mixture of tBuOH and $H_2O$ to remove the benzyl and Nap ethers and converted the azido into an amino group. The NMR data of the anomeric signals of compound 1 (not shown) are in agreement with reported values. Pentasaccharide 2, tetrasaccharide 3, and hexasaccharide 4 could easily be prepared by removal of the protecting groups of 20, 19, and 6, respectively.

Example 2: Epitope Mapping of *P. aeruginosa* Psl Using Synthetic Oligosaccharide Subunits This Example demonstrates protein conjugation of the synthetic oligosaccharide subunits produced in Example 1, and immunological assays to determine the epitopes bound by anti-Psl monoclonal antibodies.

General Procedure for S-acetylthioglycolylamido Derivatization of the Aminopropyl Spacer.

S-acetylthioglycolylamido derivitization of the amino propyl group of compounds 1 to 4 in FIG. 1B was carried out as follows. The oligosaccharide 3 (5.0 mg, 7.07 μmol) was slurried in dry DMF (500 μL) and S-Acetylthioglycolic acid pentafluorophenyl ester (SAMA-OPfp) (3.2 mg, 10.60 μmol) was added followed by dropwise addition of N,N-Diisopropylethylamine (DIPEA) (2.5 μL, 14.14 μmmol). After stirring at room temperature for 2 h, the mixture was concentrated, co-evaporated twice with toluene, and the residue purified by size-exclusion chromatography (Biogel P2 column, eluted with $H_2O$ containing 10% methanol) to give, after lyophilization, the corresponding thioacetate (5.2 mg, 6.36 μmol, 90%) as a white powder. In this manner, the thioacetamido derivatives of compounds 1-4 were prepared in yields of 85-90%.

General Procedure for S-Deacetylation.

S-deacetylation of the thioacetate derivatives prepared as described above was performed as follows. 7% $NH_3$ (g) in DMF solution (300 μL) was added to a solution of the thioacetate derivative corresponding to tetrasaccharide 3 (1.2 mg, 1.43 mmol) in $ddH_2O$ (40 μL) and the mixture was stirred under argon atmosphere. The reaction was monitored by MALDI-TOF showing the product peak of $[M+Na]^+$. After 1 h, the solvent was evaporated under reduced pressure. The thiol derivatized trisaccharide was further dried under high vacuum for 30 min and then used immediately in conjugation without further purification. Deacetylation of the other three oligosaccharide subunits was carried out similarly.

General Procedure for the Conjugation of Thiol Derivatized Oligosaccharides to BSA-Maleimide.

The conjugations were performed as instructed by Pierce Endogen Inc. In short, the thiol derivative (2.5 eq. excess to available MI-groups on the protein), deprotected just prior to conjugation as described above, was dissolved in $ddH_2O$ (100 μL) and added to a solution of the maleimide activated protein (2 mg) in conjugation buffer sodium phosphate pH 7.2 containing EDTA and sodium azide (200 μL). The mixture was incubated at room temperature for 18 h and then purified by Millipore Centriplus centrifugal filter devices with a 10 kDa molecular cutoff. All centrifugations were performed at 4° C. for 25 min, 3000 rpm. The reaction mixture was centrifuged and the filter washed with sodium phosphate buffer pH 7.4 (3×200 μL). The conjugate was retrieved and taken up in sodium phosphate buffer pH 7.4, 0.15 M sodium chloride (1 mL). This gave glycoconjugates with a molar carbohydrate/BSA ratio of 7:1 for tetrasaccharide 3, 8:1 for pentasaccharide 2, 15:1 for hexasaccharide 4, and 5:1 for decasaccharide 1 as determined by quantitative monosaccharide analysis by HPAEC/PAD and the Lowry protein concentration assay.

ELISA.

ELISA plates (Nunc MaxiSorp) were coated overnight at 4° C. with 3-fold serial dilutions of oligosaccharide-BSA conjugates (relative to the concentration of the conjugated oligosaccharides) followed by washing with PBS supplemented with 0.1% Tween 20 (PBS-T) and blocking with PBS supplemented with 1% bovine serum albumin (PBS-B). The coated ELISA plates were incubated with anti-Psl antibodies (5 μg/mL in PBS-B) for 1 h at 4° C. Next the plates were washed with PBS-T and treated with HRP-conjugated anti-human secondary antibodies for 1 h followed by development and analysis as described (Digiandomenico, A., et al., *J. Exp. Med.* 2012, 209, 1273-1287).

Immunological Studies.

Classification of anti-Psl monoclonal antibodies into three epitope groups based on competition assays was described in Digiandomenico, A., et al., *J. Exp. Med.* 2012, 209, 1273-1287 and PCT/US2012/041538, filed Jun. 8, 2012. The classifications are shown in Table 1 above.

After confirming the structural integrity of the synthetic Psl oligosaccharides, the ability of various anti-Psl mAbs to recognize the synthetic oligosaccharides was examined as follows. For these experiments, oligosaccharides were conjugated to BSA to facilitate coating of ELISA plates followed by testing reactivity with a representative antibody that bound each epitope class (class I—Cam-003; class II—WapR-001; class III—WapR-016).

As depicted in FIG. 3A-D, the representative class II mAb, WapR-001, reacted potently with each oligosaccharide indicating the class II anti-Psl epitope resides within the tetrasaccharide and does not require the branched mannoside of the Psl repeating unit. Since Psl is a repetitive heteropolymer, each Psl pentasaccharide subunit would serve as a target for the antibody. While not wishing to be bound by theory, this feature likely explains the potent reactivity of the class II antibodies that was previously observed for endogenous Psl purified from *P. aeruginosa*. The class III antibody, WapR-016, did not bind the tetra- (3) or pentasaccharide (2); however it did react potently with the hexasaccharide 4 and weakly with the decasaccharide 1. These results suggested that a terminal glucoside, which is uniquely contained within hexasaccharide 4, is important for optimal binding of the class III antibody. In addition, this observation suggested that the natural Psl repeating unit terminates in the branched glucoside.

The representative class I mAb Cam-003, which was previously shown to be the most functionally active and protective anti-Psl mAb against *P. aeruginosa*, did not bind any of the synthetic oligosaccharides indicating the full class I Psl epitope does not reside within the synthetic compounds. These results were unexpected since the decasaccharide 1 was presumed to contain all possible substructures of the repeating pentasaccharide. This observation raises the possibility that the class I mAb binds to a conformational epitope or a yet to be elucidated sub-stoichiometric Psl isoform. The potential for the latter is supported by the observation that mild alkaline, but not exhaustive protease treatment, during carbohydrate purification abolishes Cam-003 reactivity while maintaining WapR-001 and WapR-016 reactivity (data not shown).

The disclosure is not to be limited in scope by the specific embodiments described which are intended as single illustrations of individual aspects of the disclosure, and any compositions or methods which are functionally equivalent are within the scope of this disclosure. Indeed, various modifications of the disclosure in addition to those shown and described herein will become apparent to those skilled in the art from the foregoing description and accompanying drawings. Such modifications are intended to fall within the scope of the appended claims.

All publications and patent applications mentioned in this specification are herein incorporated by reference to the same extent as if each individual publication or patent application was specifically and individually indicated to be incorporated by reference.

What is claimed is:

1. A method comprising

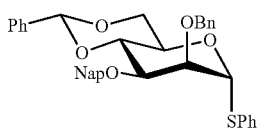
7

(a) reacting a thiomannosyl donor 7 with acceptor

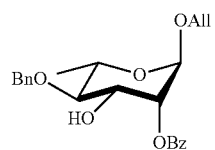
10

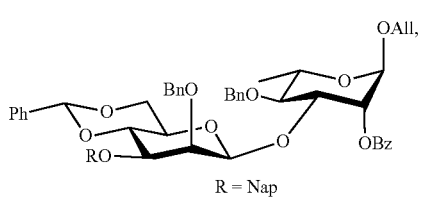
13 saccharide 10 to form disaccharide 13, and then partially deprotecting disaccharide 13 to form disaccharide 14:

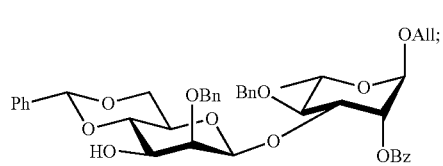
14

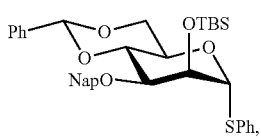
8

(b) reacting disaccharide 14 and with thiomannoside 8

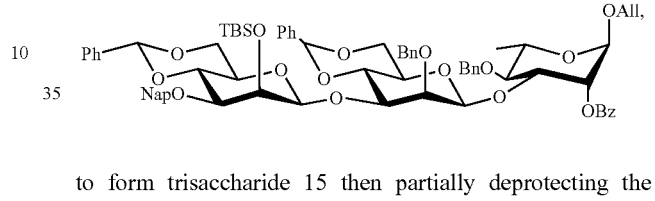
15 to form trisaccharide 15 then partially deprotecting the trisaccharide to form compound 16,

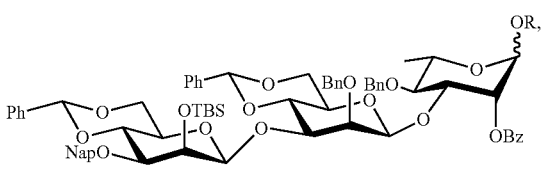
R = H then reacting compound 16 with $CCl_3$ CN, and $Cs_2 CO_3$, in dichloromethane to form the trichloroacetimidate trisaccharide 17:

and

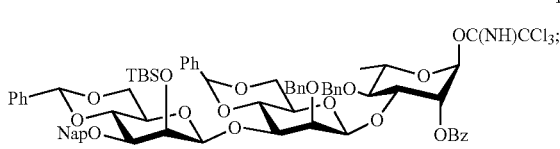
17

(c) reacting the trichloroacetimidate trisaccharide 17 with compound 12

in the presence of trimethylsilyl trifluoromethanesulfonate and dichloromethane at −30° C. to form a linear tetrasaccharide 18

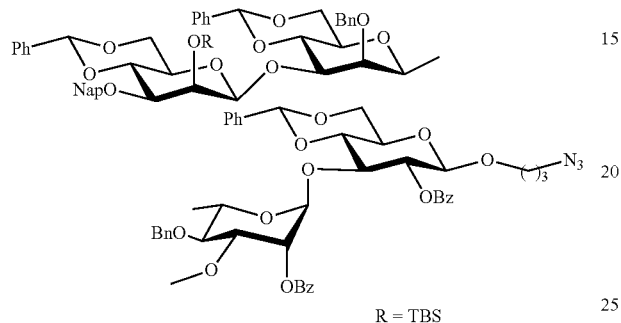

then partially deprotecting linear tetrasaccharide 18 with hydrofluoric acid in pyridine to form the linear tetrasaccharide 19:

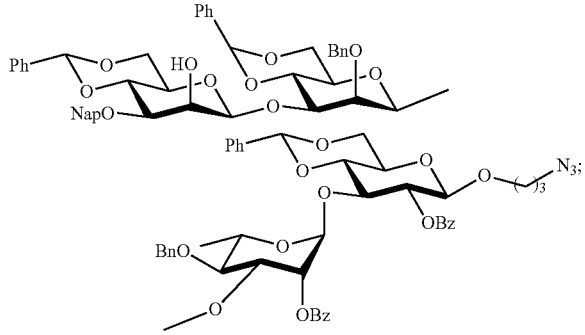

and wherein Nap is 2-methylnaphthyl, Ph is a phenyl group, Bn is a benzyl group, Bz is a benzoyl group, All is allyl ether, and TBS is t-butyldimethylsilyl.

2. The method of claim 1, further comprising deprotecting the linear tetrasaccharide 19 to form tetrasaccharide 3:

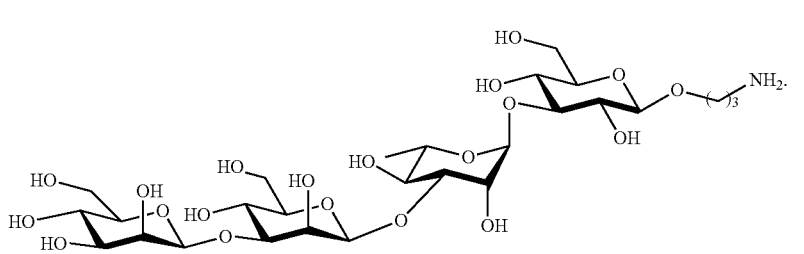

3. The method of claim 1, further comprising
(d) reacting the linear tetrasaccharide 19 with compound 9

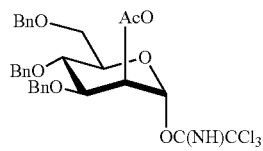

in the presence of trimethylsilyl trifluoromethanesulfonate and dichloromethane to form a pentasaccharide 20 then partially deprotecting

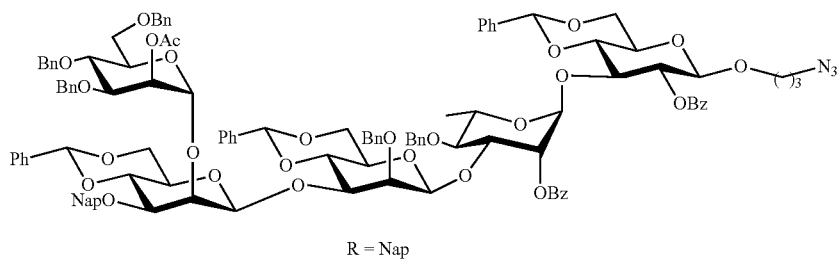

pentasaccharide 20 to form a pentasaccharide 21:

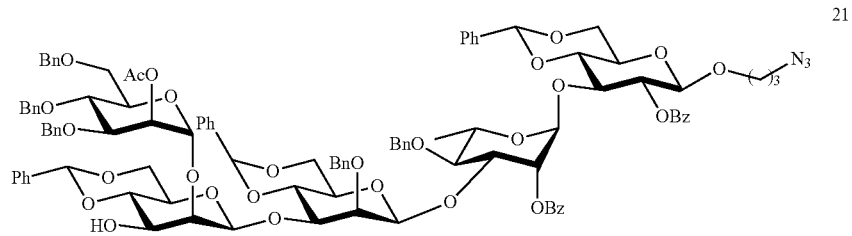

wherein Ac is an acetyl group.

4. The method of claim 3, further comprising deprotecting the pentasaccharide 20 to form a pentasaccharide 2:

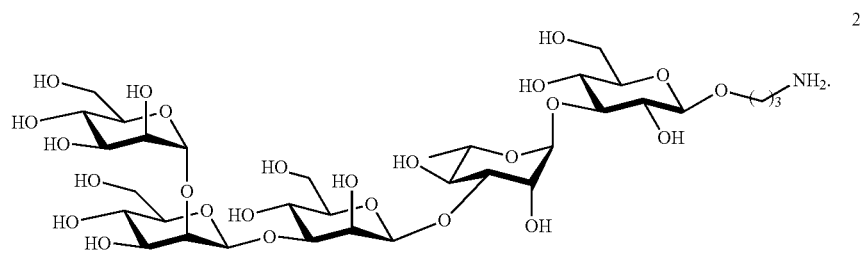

5. The method of claim 3, further comprising
(e) reacting the pentasaccharide 21 with compound 11

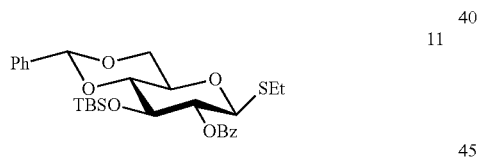

in the presence of N-iodosuccinimide, trimethylsilyl trifluoromethanesulfonate and dichloromethane to form a hexasaccharide 22

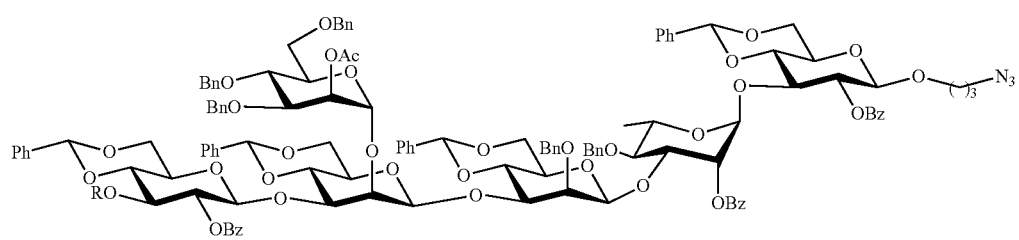

R = TBS then partially deprotecting the hexasaccharide 22 with hydrofluoric acid in pyridine to form a hexasaccharide 6:

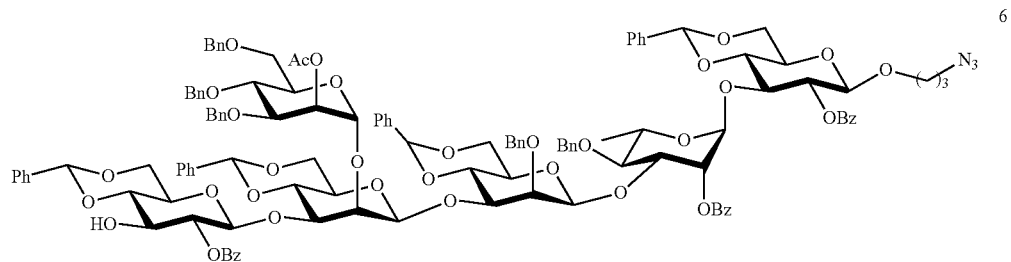

wherein Et is an ethyl group.

6. The method of claim 5, further comprising deprotecting compound the hexasaccharide 6 to form a hexasaccharide 4:

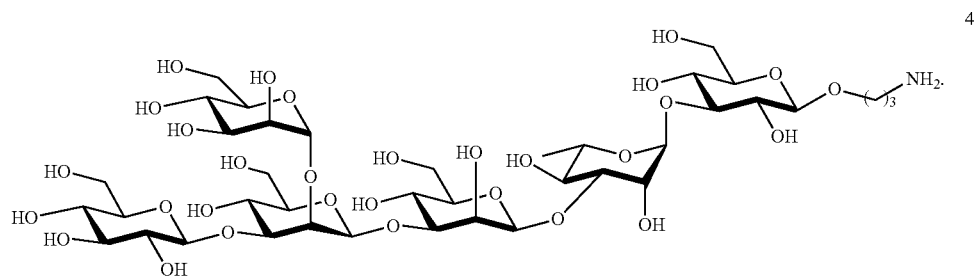

7. The method of claim 5, further comprising:

(f) partially deprotecting the trisaccharide 15 in the presence of hydrofluoric acid

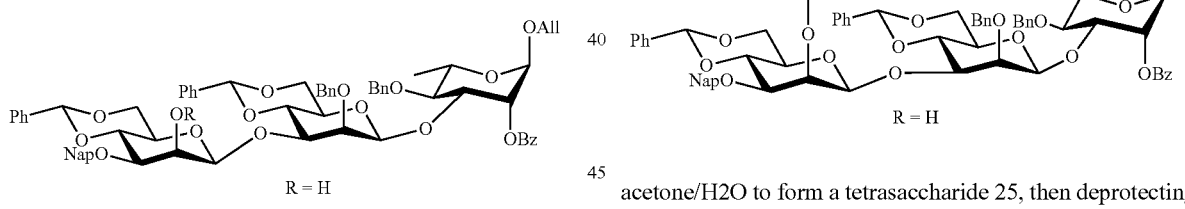

in pyridine to form a trisaccharide 23 and reacting the trisaccharide 23 with compound 9 in the presence of trimethylsilyl trifluoromethanesulfonate and dichloromethane to form a tetrasaccharide 24 then reacting the tetrasaccharide 24

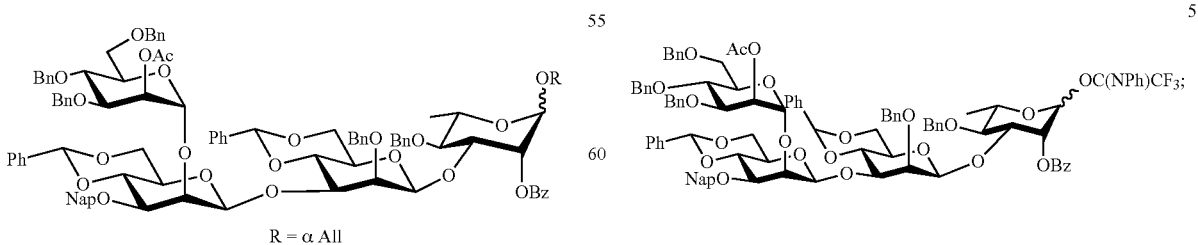

in the presence of (Ph$_3$P)$_3$RhCl, N,N-disopropylethylamine in toluene, followed by HgO, HgCl$_2$, in acetone/H2O to form a tetrasaccharide 25, then deprotecting the tetrasaccharide 25 with 2,2,2-trifluoro-N-phenylacetimidoyl chloride, 1,8-diazabicyclo[5.4.0]undec-7-ene (DBU) in dichloromethane to form a tetrasaccharide 5:

(g) reacting hexasaccharide 6 with tetrasaccharide 5 in the presence of trimethylsilyl trifluoromethanesulfonate and dichloromethane to form a decasaccharide 26 then deprotecting decasaccharide 26 to form compound 1:

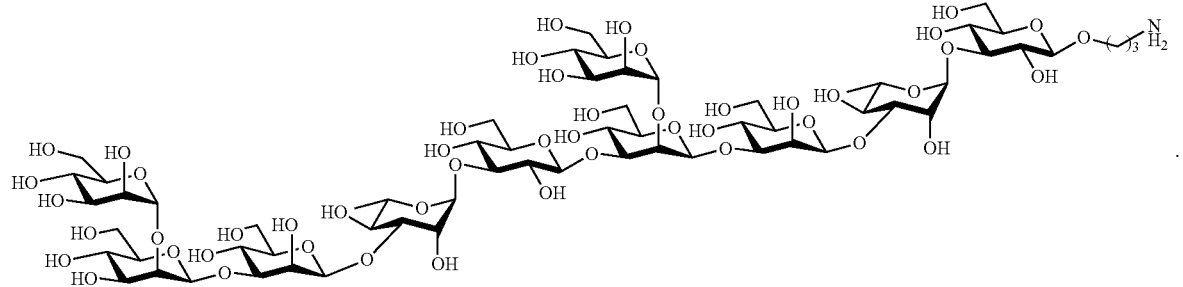
* * * * *